United States Patent [19]

Oswald

[11] 4,136,103
[45] * Jan. 23, 1979

[54] SUBSTITUTED TETRAALKYL PHOSPHONIUM ALUMINOSILICATES

[75] Inventor: Alexis A. Oswald, Mountainside, N.J.

[73] Assignee: Exxon Research & Engineering Co., Florham Park, N.J.

[*] Notice: The portion of the term of this patent subsequent to Dec. 30, 1992, has been disclaimed.

[21] Appl. No.: 839,749

[22] Filed: Oct. 5, 1977

Related U.S. Application Data

[63] Continuation-in-part of Ser. No. 644,810, Dec. 29, 1975, Pat. No. 4,053,493, which is a continuation-in-part of Ser. No. 402,465, Oct. 1, 1973, Pat. No. 3,929,849.

[51] Int. Cl.$^2$ ............................................. C07F 5/06
[52] U.S. Cl. .................................................. 260/448 C
[58] Field of Search ................................... 260/448 C

[56] References Cited

U.S. PATENT DOCUMENTS

| 2,531,427 | 11/1950 | Hauser | 260/448 C |
|---|---|---|---|
| 2,859,234 | 11/1958 | Clem | 260/448 C |
| 2,966,506 | 12/1960 | Jordan | 260/448 C |
| 3,014,871 | 12/1961 | Fulton et al. | 260/448 C |
| 3,929,849 | 12/1975 | Oswald | 260/448 C |
| 4,053,493 | 10/1977 | Oswald | 260/448 C |

OTHER PUBLICATIONS

Intercalation and Catalytic Activity of Metal Complexes, in Mica-Type Layered Silicates, Quayle and Pinnavaia Preprints, Div. Petr. Chem. Inc. pp. 1217-1219 (1977).

Primary Examiner—Helen M. S. Sneed
Attorney, Agent, or Firm—Joseph J. Allocca

[57] ABSTRACT

Novel layer type clay-like tetraalkyl phosphonium aluminosilicates can be produced by the ion exchange reaction of metal aluminosilicates with phosphonium salts. For example, layered type tetraalkyl phosphonium derivatives of clays are prepared by the reaction of sodium clays with tetraalkyl phosphonium chlorides. Substituted tetraalkyl phosphonium clays such as phosphino-, amino-, cyano- and hydroxy-alkyl derivatives are similarly synthesized. The novel compositions have unexpected microstructure, thermal stability, and thixotropic properties in organic liquids.

27 Claims, No Drawings

SUBSTITUTED TETRAALKYL PHOSPHONIUM ALUMINOSILICATES

CROSS-REFERENCE TO RELATED APPLICATIONS

The present application is a continuation-in-part of U.S. Patent Application of Ser. No. 644,810 filed Dec. 29, 1975, now U.S. Pat. No. 4,053,493 which in turn is a continuation-in-part of U.S. Patent Application of Ser. No. 402,465 which was filed on Oct. 1, 1973 and issued as U.S. Pat. No. 3,929,849 on Dec. 30, 1975.

FIELD OF THE INVENTION

This invention is related to novel quaternary onium aluminosilicates, namely layered type tetraalkyl phosphonium aluminosilicates, their preparation, structure and properties. More particularly, this invention relates to tetraalkyl phosphonium derivatives of clays of layered structure having a high ion exchange capacity. Specifically, this application relates to phosphinoalkyl, aminoalkyl, cyanoalkyl and hydroxyalkyl phosphonium clays.

These phosphonium clays in general are related to tetraalkyl ammonium montmorillonite clays known in the trade as organic Bentones, but they have unexpected interlayer structures, are thermally more stable and, dependent on their structure, show superior thixotropic properties in organic liquids of varying polar character.

PRIOR ART VERSUS THE PRESENT INVENTION

The affinity between certain organic compounds and clays has been known for many years. J. U. Lloyd reported the adsorptive capacity of Fuller's earth for alkaloids in 1916 in the *Journal of the American Pharmaceutical Association*, Volume 5, pages 381 to 390 and 490 to 495. C. R. Smith reacted organic bases and their salts with bentonite and presented evidence that the reaction involved ion exchange. (For reference see the *Journal of the American Chemical Society*, Volume 56, pages 1561-1563, from the year 1934).

Quaternary phosphonium derivatives of water dispersible clays were mentioned in the patent literature under the term "onium clays". Onium clays were claimed for various uses in U.S. Pat. Nos. 2,531,396; 2,531,427; 2,531,440; 2,531,812; 2,662,987; 3,671,190. The word "onium" is a cumulative term for ammonium phosphonium, arsonium, stibonium, oxonium, sulfonium and selenonium. However, the above patents covering onium clays were specifically directed towards ammonium clays. Among tens of thousands of the possible phosphonium clays, only the triphenyl dodecyl phosphonium derivative was mentioned. The only reference to a layered quaternary tetraalkyl phosphonium clay is to dimethyl dioctadecyl phosphonium bentonite in U.S. Pat. No. 2,895,954. However, this reference was apparently made by accident without any knowledge of the subject matter as indicated by disclosures of the nonexistent dimethyl dioctadecyl oxonium and sulfonium bentonites in the same patent. The existence of the latter compounds would clearly violate the generally valid chemical valence rules, since oxonium and sulfonium ions have only three covalent bonds. It is clear from the disclosure that the inventor used purchased dimethyl dioctadecyl ammonium bentonite to gel bituminous compositions. With regard to other "dimethyl dioctadecyl onium compounds" he had an apparently incorrect assumption. Another reference in U.S. Pat. No. 3,709,979 is to tetrabutyl phosphonium zeolite, i.e., an aluminosilicate having a hole and tunnel type structure.

Although the prior art descriptions of onium clays had no structural limitations, they were generally limited to compositions which gel hydrocarbons or are used as intermediates. For gelling, it was generally assumed that the onium moiety should contain at least ten carbon atoms in a straight chain. See U.S. Pat. No. 2,531,426 by E. A. Hauser. Furthermore, it was claimed that the clay should have an ion exchange capacity of at least 25 miliequivalent onium ion per 100 g.

In contrast, to the all inclusive disclosures of the patent literature very few onium clays were found useful in practice. All the commercial onium clays are quaternary ammonium derivatives. For many years, dimethyl dioctadecyl ammonium bentonite was the only commercial compound in the field. For references, see J. W. Jordan and F. J. Williams, *Organophylic Bentonites* III, *Kolloid Zeitschrift*, Volume 137, pages 40 to 48, 1954; J. V. Kennedy and W. T. Granquist, "Flow Properties of Dispersions of an Organo Montmorillonite in Organic Media", *Nat. Lub. Grease Inst. Spokesman*, Volume 29, No. 5, pages 138-145, 1965. More recently, dimethyl octadecyl benzyl ammonium bentonite was introduced. These two clays were useful in gelling a large variety of liquid hydrocarbons. However, they were ineffective in highly polar nonhydrocarbons such as polyesters.

The present invention is the result of a long range study of tetraalkyl phosphonium clays which, at first glance, appear analogous to the known tetraalkyl ammonium clays. Our study showed that the novel tetraalkyl phosphonium clays have several unobvious, inherent properties. They are thermally more stable than their nitrogen analogs. They do not require the addition of polar dispersants for gelling organic liquids. They gel nonhydrocarbons just as well as hydrocarbons. Their gelling action does not depend on the presence of at least one straight alkyl chain having a minimum of ten carbon atoms. They have a more selective interaction with liquids which is useful in various separations.

In an apparent contrast to the known quaternary tetraalkyl ammonium clays, the novel quaternary tetraalkyl phosphonium clays possess a variety of properties strongly dependent on the structure of the aliphatic substituents. In the area of ammonium clays, only the long chain alkyl and methyl substituted derivatives were synthesized. Most of these exhibited the same kind of properties. In contrast, it was found in the present invention that, dependent on the number of long chain alkyl substituents on the phosphorus, phosphonium clays show very different properties. For example, the different interplanar distance of such layered clays indicates very different structures. Furthermore, it was found that if one is to substitute ethyl, propyl and butyl groups instead of methyl, as the low trialkyl substituents of long chain monoalkyl phosphonium clays, again different microstructures and properties result.

The present invention of novel tetraalkyl phosphonium clays, of course, would not have been possible without the advance which was made in the field of phosphonium salt clay reactants since the original patent application on ammonium clays was filed in 1946, (U.S. Pat. No. 2,531,427). At that time, only a handful of tetraalkyl phosphonium salts were known. Only triphenyl alkyl phosphonium salts were available. None of them were attractive for the preparation of organo-clay gellants. In the meantime, many tetraalkyl phosphonium salts became known. Nevertheless, most of the surprisingly attractive phosphonium clay gellants of the present invention are based on novel tetraalkyl phosphonium salts. The latter were synthesized during the course of concurrent work in alkyl phosphine and phosphonium salt chemistry in the broadest context of the same long range research program which led to this invention. These novel, intermediates are (will be) covered by U.S. Pat. No. 3,998,754 and related patent applications.

In summarizing the prior art, it is pointed out that onium clays were disclosed in several patents which include all phosphonium clays ever to be made. However, there was nothing specific known about tetraalkyl phosphonium clays. In view of this and the surprising differences between tetraalkyl phosphonium clays of the present application and the known tetraalkyl ammonium clays of the prior art, the present compositions are patentably distinct from those of the prior art.

Investigations were carried out with the novel tetraalkyl phosphonium clay compositions with regard to their usefulness as thixotropic agents in various areas, as separation and complexing agents, and as reinforcing agents.

SUMMARY OF THE INVENTION

Onium clays in general, possess properties which make them compatible with organic compounds. Certain tetraalkyl ammonium clays, in particular, are effective as hydrocarbon gelling agents. The usefulness of such ammonium clays stimulated this work with the aim of discovering novel onium clays.

In the present invention, new types of tetraalkyl phosphonium clays are disclosed. Their preparation from the corresponding phosphonium salts and inorganic clays in also described. These clays have unexpected structures as determined by X-ray. Furthermore, they have unexpected properties such as thermal stability and selective interaction with organic liquids and vapors. Due to these properties, they were found surprisingly useful as thixotropic, reinforcement and separation agents.

PRODUCT COMPOSITIONS

The tetraalkyl phosphonium clay compositions of the present invention have four $C_1$-$C_{100}$ aliphatic hydrocarbyl or substituted aliphatic hydrocarbyl moieties attached to their phosphorus atom. The positive charge of the phosphonium cations of such compositions is balanced by negatively charged clay particles of various charge densities. These clays are modified natural or synthetic metal aluminosilicates.

As such tetraalkyl phosphonium clays can be defined by the formula $[R_4P^+]_e Clay^{-e}$ wherein $e$ is the number of the negative charges on the clay particle which are neutralized by phosphonium cations. Such a number is dependent on the clay particle size and as such cannot unequivocally be determined. Consequently, the simplified formula of the phosphonium clays is $[R_4P^+]$ Clay$^-$, wherein R is $C_1$-$C_{100}$ aliphatic hydrocarbyl or substituted aliphatic hydrocarbyl, preferably $C_1$-$C_{40}$ alkyl or monosubstituted alkyl. In a preferred type of phosphonium clay, at least one of the R groups is substituted aliphatic hydrocarbyl.

The term "aliphatic hydrocarbyl" includes saturated, open chain and cyclic alkyl groups. It also includes similar unsaturated, i.e., alkenyl and alkinyl groups. The substituents of the aliphatic hydrocarbons include all those moieties which are compatible. Such substituents can be aromatic groups such as phenyl and heteroaromatic groups, such as phenyl and their derivatives. They can be halogens, i.e., F, Cl, Br, I. They can represent heteroatomic radicals such as oxygen, or sulfur-containing groups, e.g. hydroxy, carbonyl, carboalkoxy, thiol, thioether, sulfone, sulfonate. They can contain nitrogen heteroatom, e.g. in the form of amino, cyano, nitrite, nitrate, amido groups. They can also contain organic silicon heteroatom, preferably as a silane. Phosphorus-heteroatom containing groups, such as phosphine oxide, phosphate, phosphite, phosphonate, phosphinate, are also included. Dependent on their character, such heteroatomic substituents may be either inserted into the aliphatic chain as ethers or can take the place of one or more hydrogens on the aliphatic carbon chain or on an aromatic moiety, as halogens do. Although the various aliphatic hydrocarbyl groups can be substituted, for many uses the unsubstituted groups are preferred. The preferred substituents however, are selected from the group consisting of phosphino-, amino-, cyano-, and hydroxy groups.

Quaternary phosphonium groups may be covalently bound by di- or polyvalent aliphatic radicals to form diphosphonium and polyphosphonium compounds. These in turn can be also converted to phosphonium clays.

Examples of the aliphatic hydrocarbyl groups include methyl, ethyl, i-propyl, t-butyl, n-dodecyl, docosyl, squalyl, triacontyl, hexatriacontyl, $C_{100}$ alkyl derived from isobutylene oligomer; cyclopentyl, cyclododecyl; vinyl, allyl, propargyl, cyclohexenyl, methylcyclopentenyl, benzyl, chlorobenzyl, phenylethyl, dodecylbenzyl, tetrahydronaphthyl, phenoxybenzyl, benzothiazylthiomethyl; chloroethyl, iodobenzyl; dichloroallyl, perfluoroundecyl, bromotetradecyl, hydroxymethyl, hydroxyethyl, hydroxypropyl, epoxypropyl, carbomethoxyethyl, hydroquinonethiomethyl, acetylbenzyl, mercaptopropyl, hexacosylthiopropyl, aminopropyl, diethylaminopropyl, triacontylaminoethyl, N-morpholinoethyl, cyanoethyl, nitrobenzyl, diphenylphosphinodecyl.

One of the preferred class of compositions has at least one, preferably three saturated, unsubstituted alkyl groups. In this class of compounds, it is furthermore preferred that the fourth aliphatic group be alkyl, alkenyl, alkinyl or monosubstituted derivative thereof.

Furthermore, it is preferred that at least one of the aliphatic hydrocarbyl groups should contain at least 8 carbon atoms. This higher aliphatic group is preferably a saturated alkyl group.

The aliphatic substituents of the phosphonium groups can be independently selected. Some of the more common selections are indicated by the tabulation on pages 217 to 467 in the monograph on *Organic Phosphorus Compounds*, edited by G. M. Kosolapoff and L. Maier, Volume 2, Chapter 4 by P. Beck, published by J. Wiley & Sons, Inc. 1972, in New York. The most common types of these selections are indicated by the formula:

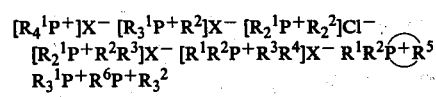

wherein $R^1$ to $R^4$ have the same meaning as P; $R^5$ and $R^6$ are divalent aliphatic radicals, preferably alkylene, alkenylene, alkinylene and their substituted derivatives in the $C_1$ to $C_{40}$ preferably $C_1$ to $C_{14}$ range.

Examples for divalent radicals are ethylene, butenylene, butinylene, cyclohexylene, octamethylene, tetradecamethylene, triacontylene, hydroxymethylethylene, o-chloroxylylene.

The preferred quaternary phosphonium groups in the simple salt form, e.g. as chlorides, are surface active. There is a correlation between the surfactant activity of the salts and the gellant activity of the clay derivatives. Consequently, detergent range n-alkyl groups are preferred phosphorus substituents for phosphonium clays.

Tetraalkyl phosphonium clays can be further classified according to the number of high and low alkyl substituents of the phosphonium group. In general, low alkyl groups mean aliphatic substituents having up to 7 carbon atoms. High alkyl groups possess a minimum of 8 carbons.

A preferred class of phosphonium clay compositions is of the following formula: $[R'_3P^+R'']$ Clay$^-$, wherein $R'$ and $R''$ are aliphatic hydrocarbyl radicals selected from the group consisting of $C_1$-$C_7$ low aliphatic radicals and $C_8$-$C_{100}$ high aliphatic radicals and their substituted derivatives in such a manner that if $R'$ is low aliphatic, $R''$ should be high aliphatic and the reverse. The high aliphatic radicals are preferably $C_8$-$C_{40}$ alkyl groups. The low unsaturated radicals are preferably selected from $C_1$-$C_7$ aliphatic radicals consisting of alkyl, alkenyl, alkinyl and monosubstituted derivatives thereof, particularly monosubstituted alkyl.

Another class of phosphonium clay compositions is represented by the formula: $[R_2'P^+R_2'']$ Clay$^-$, wherein the meaning of $R'$ and $R''$ is the same. Some of the preferred compositions of this type are wherein the $R'$ groups are $C_9$-$C_{20}$ alkyl groups, one $R''$ group is a $C_1$-$C_4$ alkyl and the other $R''$ is $C_1$-$C_4$ alkyl, $C_1$-$C_4$ monosubstituted alkyl, $C_2$-$C_4$ alkenyl, $C_2$-$C_4$ alkinyl. Even more specifically preferred compositions are those having $R'$ as $C_9$-$C_{16}$ alkyl and $R''$ as $C_1$-$C_2$ alkyl.

Among the unsubstituted tetraalkyl phosphonium clays there are also preferred high mono-, di- and trialkyl derivatives.

Preferred types of high monoalkyl phosphonium clays are of the formula:

$$[C_mH_{2m+1}P^+(C_nH_{2n+1})_3] \text{ Clay}^-$$

wherein m is 12 to 40, more preferably, 16 to 30, most preferably 20 to 30 and n is 1 to 4, preferably 3 to 4.

Preferred types of higher dialkyl phosphonium clays are of the formula:

$$[(C_rH_{2r+1})_2P^+(C_sH_{2s+1})_2] \text{ Clay}^-$$

wherein r is 8 to 40, preferably 14 to 20, most preferably 18, s is 1 to 7, preferably 1 to 4. Preferably at least one of the two low alkyl groups is other than methyl.

Preferred types of higher trialkyl phosphonium clays are of the formula:

$$[C_kH_{2k+1}P^+(C_jH_{2j+1})_3] \text{ Clay}^-$$

wherein j is 6 to 40, preferably 8 to 18; most preferably 8, 9 or 16 to 18, k is 1 to 4, preferably 4.

The high alkyl phosphonium clays of the present invention include as preferred compositions, those of unsymmetrical structure. Specifically, preferred unsymmetrical high monoalkyl phosphonium clays are those of the formula:

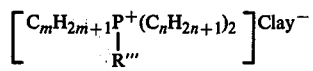

wherein $R'''$ is a $C_1$ to $C_4$ aliphatic hydrocarbyl, preferably a $C_1$ to $C_4$ alkyl group different from $C_nH_{2n+1}$. It is most preferred that $R'''$ be methyl or ethyl. Similarly, preferred unsymmetrical high dialkyl phosphonium clays are of the formula:

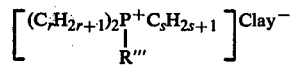

wherein the meaning of $R'''$, s and r are as above.

Another preferred type of higher alkyl phosphonium clays has at least one unsaturated low hydrocarbyl, preferably allylic substituent. Specifically, preferred classes of compounds are of the formula:

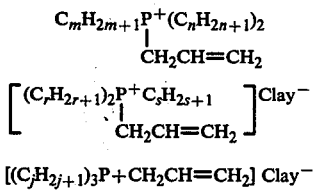

$$[(C_jH_{2j+1})_3P^+CH_2CH=CH_2] \text{ Clay}^-$$

Similar phosphonium clays having a reactive substituent may have acrylate, hydroxy, thiol, amino, silane, halogen, cyano, styryl and other similar functional groups.

Preferred type of tetraalkyl phosphonium clays have at least one substituent on at least one of the alkyl chains. Such a substituent is preferably selected from the group consisting of phosphino, amino, cyano and hydroxy substituents. The phosphino group is preferably $C_1$-$C_{40}$ dihydrocarbyl phosphino, more preferably diaryl phosphino, most preferably diphenyl phosphino. The amino group is preferably —$NH_2$, $C_1$-$C_{40}$ alkylamino and dialkylamino, more preferably, $C_2$-$C_{18}$ dialkylamino. The phosphino group can be free or complexed with transition metal compounds.

The total number of carbon atoms of each alkyl group of the above-substituted tetraalkyl phosphonium salts is $C_1$-$C_{100}$ as previously stated. It is preferred that at least one of these alkyl groups contain at least 8 carbon atoms. This higher aliphatic group is preferably a saturated, nonsubstituted alkyl group.

The divalent aliphatic group bridging the phosphonium phosphorus and the substituting group can possess from one to forty carbons. It can be either a low aliphatic group of the $C_1$-$C_7$ range or a higher aliphatic group, preferably in the $C_8$-$C_{40}$ range. In most cases, it is preferred that the substituting group be on the low aliphatic group. A preferred class of low aliphatic groups includes $C_1$-$C_6$ divalent alkylene and alkenylene groups. The higher aliphatic groups are preferably of the polymethylene type.

Besides the higher alkyl and the substituted alkyl groups, this type of phosphonium clays may preferably contain an unsaturated low alkyl group, most preferably, an allylic group.

Accordingly, the general formulae of this preferred type of substituted tetraalkyl phosphonium clays are:

$$\{R_xP^+[QZ]_y\}Clay^-$$

wherein R is a $C_1-C_{100}$ monovalent aliphatic hydrocarbyl radical, preferably $C_1-C_{100}$ aliphatic hydrocarbyl radical selected from the group consisting of alkyl and alkenyl, more preferably, a $C_1-C_{100}$ alkyl, most preferably at least one R is a $C_2-C_{10}$ aliphatic hydrocarbyl; Q is a $C_1-C_{100}$ divalent aliphatic hydrocarbyl radical, preferably a $C_1-C_{40}$ divalent aliphatic radical selected from the group consisting of alkylene and alkenylene; Z is a heteroatomic radical containing up to 40 carbon atoms preferably selected from the group consisting of phosphino, amino, cyano and hydroxy groups, more preferably selected from the group consisting of diphenyl phosphino, $-NH_2$, $C_4-C_{18}$ dialkylamino, wherein x and y are 1 to 3, preferably 1 or 3, providing that x plus y equals 4.

If there are several R groups, they are independently selected. It is preferred that at least one of the R groups be a $C_8-C_{100}$ high aliphatic hydrocarbyl radical, preferably alkyl radical and be unsubstituted. The rest of the R groups are preferably $C_1-C_7$ low aliphatic hydrocarbyl radicals, more preferably selected from the group of alkyl and alkenyl radicals, most preferably alkyl radicals. There is a specific preference for compounds wherein the low aliphatic hydrocarbyl radicals are alkyl except one which is a $C_3-C_5$ allylic radical, most preferably allyl.

A preferred subgeneric composition comprises diphenylphosphino substituted tetraalkyl phosphonium clays of the formula:

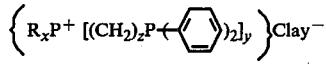

wherein z is 1 to 40, preferably 6 to 14 and the other symbols are as previously defined.

Another preferred subgeneric composition comprises amino substituted tetraalkyl phosphonium clays of the formula:

$$\{R_xP^+[(CH_2)_zN(C_qH_{2q+1})_2]_y\}Clay^-$$

wherein q is 0 to 18, preferably 1-18, more preferably 2-18, most preferably 2-4; and the other symbols are as previously defined except that the most preferred value of z is 3.

A third preferred subgeneric composition comprises cyano-substituted tetraalkyl phosphonium clays of the formula:

$$\{R_xP^+[(CH_2)_zCN]_y\}Clay^-$$

wherein the symbols are as previously defined, the most preferred value of z being 2.

A fourth preferred subgeneric composition comprises hydroxy substituted tetraalkyl phosphonium clays of the formula:

$$\{R_xP[(CH_2)_zOH]_y\}Clay^-$$

wherein the symbols are as previously defined, the specifically preferred range of z being 1 to 3.

Examples of the unsubstituted aliphatic phosphonium groups on clays include docosyl trimethyl phosphonium, hexatriacontyl tricyclohexyl phosphonium, octadecyl triethyl phosphonium, docosyl triisobutyl phosphonium, methyl trinonyl phosphonium, ethyl trihexadecyl phosphonium, dimethyl didecyl phosphonium, diethyl dioctadecyl phosphonium, octadecyl diethyl allyl phosphonium, trioctyl vinylbenzyl phosphonium, octyl nonyl decyl propargyl phosphonium, bis-trioctyl ethylene diphosphonium, bis-(diethyloctadecyl) xylylene diphosphonium, etc.

Examples of the phosphine substituted aliphatic phosphonium groups on clays include diphenylphosphinodecyl dihexadecyl methyl phosphonium, ditolylphosphinoethyl benzyl trioctyl phosphonium, dibiphenylylphosphinohexyl docosyl i-butyl methyl phosphonium, tris-diphenylphosphinopropyl benzyl phosphonium, bis-cyclohexylphosphinotetradecyl trimethyl phosphonium, bis-t-butylphosphinoethylphenyl ethyl trimethyl phosphonium.

Examples of the amine substituted aliphatic phosphonium groups on clays are the following: tris-aminopropyl docosyl phosphonium, bis-diethylaminotetradecyl, eicosyl ethyl phosphonium, diisopropylaminopropyl diisobutyl benzyl phosphonium, phenylethylaminoundecyl dicyclohexyl methyl phosphonium, tris-benzylaminopropyl dodecyl phosphonium, trioctyl dimethylaminopropyl phosphonium.

Examples of the cyano-substituted aliphatic phosphonium groups on aluminosilicates are the following: tris-cyanoethyl hexadecyl phosphonium, bis-cyanopropyl dodecyl allyl phosphonium, cyanododecyl trinonyl phosphonium, bis-(triscyanoethyl) ethylene diphosphonium, cyanoethyl dodecyl dicyclohexyl phosphonium, triacontyl tris-cyanoethyl phosphonium.

Examples of the hydroxy substituted phosphonium groups of clays are: tris-hydroxymethyl tetracosyl phosphonium, tris-hydroxyethyl dodecylbenzyl phosphonium, tris-hydroxypropyl octadecyl phosphonium, hydroxypropyl trioctyl phosphonium, hydroxyethyl dicyclohexyl crotyl phosphonium, hydroxydecyl triethyl phosphonium, eicosyltrihydroxymethyl phosphonium.

Examples of miscellaneous substituted phosphonium groups clay substituents are: triisobutyl perfluoroundecyl phosphonium, tris-acetoxyethyl docosyl phosphonium, tris-carbamidoethyl dodecyl phosphonium, tris-carboxyethyl hexadecyl phosphonium, tris-carboethoxyethyl eicosyl phosphonium, dichlorobenzyl diethyl docosyl phosphonium, dibromobenzyl trioctyl phosphonium, tris-chloroallyl eicosyl phosphonium, tris-thiopropyl dodecylbenzyl phosphonium, trimethylsilyldodecyl diisobutyl decyl phosphonium, tris-dibromoallyl benzyl phosphonium.

The modified $Clay^-$ groups of the present phosphonium compositions are best defined in terms of the layer type natural and synthetic metal and ammonium aluminosilicates from which they are derived.

The natural clay starting materials of the present invention are fine grained metal aluminosilicates which develop plasticity when mixed with limited amounts of water. For a more detailed definition and classification of clays, see the monograph entitled *Clay Mineralogy* by R. E. Grim, published by McGraw-Hill, Inc., New York, in 1968, particularly Chapters 1 to 3 on pages 1 to 50. Similar synthetic clay derivatives are also included. Preferred synthetic clay-like minerals are described in U.S. Pat. No. 3,671,190.

In general, sodium aluminosilicate clays are preferred for the derivation of the present phosphonium clays. The preferred clays have high cation exchange capacities and are crystalline. Among the preferred clays are those having crystalline layer type structures. For example, the three-layer type sodium montmorillonite clays can be advantageously used. Synthetic montmorillonites, e.g. laponites, are also suitable. Another useful clay is the chain structure type attapulgite. Two layer type clays such as kaolinites can be also used. Zeolites, i.e., metal or ammonium aluminosilicates having a tunnel-hole structure, are not included in the term "clay" as it is used in the present invention.

Further examples of clays are halloysite, smectite, illite, vermiculite, chlorite, sepiolite, palygorskite, saponite, montronite, muscovite, beidellite, biotite, micas, talcum, batavite, allevardite, stevensite, amesite.

PROCESS OF PRODUCT PREPARATION

The above described clays, i.e., metal aluminosilicates, particularly the more reactive ammonium and sodium aluminosilicate clays, are used as starting materials in the present process. These clays are reacted with tetraalkyl phosphonium salts to form the corresponding quaternary phosphonium salt products. The phosphonium salt reactants are of the formula: $y[R_4P^+] X^{-y}$, wherein y is the number of the valency of the anion, i.e., 1 to 5, preferably 1 to 3; most preferably 1 X is an anion, preferably an anion derived from protic acids. Examples of X are halogen, i.e., chlorine, bromine, fluorine, iodine, sulfate, sulfonate, phosphate, phosphonate, phosphite, carboxylate, such as acetate.

The clay starting materials are usually reacted in the form of a suspension. The preferred suspending agent is water. Aqueous alcohols can be also used. The lower alcohols, having 1 to 3 carbon atoms, can be also used. It may be advantageous at times to use a hydrocarbon such as heptane, together with the aqueous medium, since the phosphonium clay products are usually more compatible with hydrocarbons than water.

The phosphonium salt reactants can be added to the clay suspension as such or as a solution. Suitable exemplary solvents are water, alcohols, ketones, hydrocarbons. A water miscible solvent is usually preferred. On the addition of the phosphonium salt to the clay, ion exchange takes place. If the $X^-$ anion of the salt and the Me cations of the clay are monovalent, the reaction can be simply described by the following scheme:

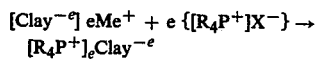

wherein Me is metal, ammonium, hydrogen, preferably metal.

This reaction can be carried to full or partial conversion. The term "full conversion" means that all the exchangeable metal cations are exchanged for phosphonium cations. The amount of exchangeable metals is usually given in miliequivalents per 100 g clay and is designated as ion exchange capacity. The amount of phosphonium salt may exceed the ion exchange capacity of the clay. In such cases, the "excess" phosphonium salt is complexed with the phosphonium clay.

An advantageous method for the preparation of the tetraalkyl phosphonium clays consists of adding the corresponding phosphonium salt to an aqueous suspension of the clay. The phosphonium salt is preferably added as a solution in water or in alcohol. As a result of the ion exchange, the clay usually becomes less hydrophylic and precipitates from the water. The metal salt by-product of the exchange is usually water soluble. Consequently, the tetraalkyl phosphonium clay products can be usually separated as crystalline solids by simple filtration and washing.

The ion exchange reaction is rather independent of the reaction temperature. The temperature is preferably above the crystallization point of the medium and below its boiling point. For aqueous systems the temperature is between 0 and 100° C., preferably between 40° and 80° C.

The occurrence of the reaction is also rather independent of the concentration of the reactants. The ion exchange goes to completion even in extremely dilute media. Nevertheless, if the reaction is carried out for manufacturing purposes, practicality commands a lower limit of reactant concentration at about 0.1%. The higher limit is usually set by the viscosity a of the thixotropic clay suspension, usually at 7.0%. The preferred clay concentrations are in the range of 0.5 and 10%. It is most often preferred to operate in the 1 to 5% clay concentration range. The concentration of the phosphonium salt when added is immaterial. The only significance of the solvent here is in aiding the mixing with the clay suspension and adjusting the final solvent concentration in the reaction mixture.

PRODUCT PROPERTIES

The tetraalkyl phosphonium clays of the present invention have many unexpected properties. Some of these properties are common to all the products and distinguish them from analogous tetraalkyl ammonium clays. Other unexpected properties are dependent on the presence of particular aliphatic substituents. A general discussion of these properties will be provided in the following.

The thermal stability of all the tetraalkyl phosphonium clays is greater than that of their ammonium analogs. The difference in thermal stability became apparent when the quaternary clay samples were heated up to 900° C. at a certain rate under nitrogen. Under these conditions, the temperature and the rate of the weight loss of the sample reflect its thermal stability. Such studies showed that the phosphonium clays on an average suffered comparable weight loss at temperatures about 80° C. higher than those observed for the ammonium analogs at the same heating rate. Furthermore, it was found that tetraalkyl phosphonium clays having higher than methyl substituents were thermally more stable under these conditions than similar derivatives having methyl substituents.

The affinity of tetraalkyl phosphonium clays towards polar compounds is higher than that of their nitrogen analogs. This property may be connected with more facile, and more stable complex formation in the case of the phosphonium clays. Due to this, tetraalkyl phosphonium clays are more active gelling agents for polar organic compounds such as aromatic hydrocarbons, and oxygenated compounds. Also, tetraalkyl phosphonium clays do not require polar additives as the ammonium analogs do when used as gelling agents.

The above affinity is responsible for the comparatively long retention of aromatics when passed through gasliquid chromatography (glc) columns packed with phosphonium clays. Furthermore, probably for the same reason, silicon modifiers are not necessary when phosphonium rather than ammonium clays are used in such glc separations.

There are also unexpected differences between the microstructure of the various types of quaternary tetraalkyl phosphonium clays. This microstructure refers to the orientation of the quaternary phosphonium groups between the inorganic aluminosilicate layers. The repeat distance of these layers in the original clays and in their various quaternary derivatives could be determined by X-ray. Comparing these distances, the changes of the interlayer distances could be determined. It was found that the increase of these distances could be directly related to the carbon number of the higher n-alkyl substituents on the phosphorus. Furthermore, it was surprisingly found that these distances also depend on the number of higher n-alkyl groups per phosphorus atoms. Obviously the orientation of the phosphonium groups and particularly the orientation of the higher n-alkyl substituents depends on the number of higher n-alkyl groups per phosphorus.

The above dry microstructure of the quaternary higher monoalkyl phosphonium clays is such that the interplanar spacing is moderately influenced by the number of carbons of the n-alkyl groups. Such a moderate effect can be visualized by the orientation of alkyl groups at a small angle to the aluminosilicate plane. In the case of quaternary higher dialkyl phosphonium clays, this effect on the spacing of the number of carbons per n-alkyl group is more pronounced. Accordingly, a larger angle between the n-alkyl groups and the layer plane is assumed. In the case of the quaternary higher trialkyl phosphonium clays, this effect is even higher and can be explained by a perpendicular orientation of the higher n-alkyl groups.

As a consequence of the above microstructures, the required number of carbon atoms per higher n-alkyl substituent for gelling is much smaller for higher trialkyl than higher monoalkyl phosphonium clays. Furthermore, due to this structure, $C_{1-3}$ alkyl $C_{7-9}$ trialkyl phosphonium montmorillonites are especially capable of interacting with highly polar groups such ester groups. On the other hand, quaternary phosphonium compounds having only one $C_{12}$ or higher alkyl groups per phosphonium moiety are particularly apt to interact with hydrocarbons such as toluene.

Thus, the gelling properties of the layered high alkyl phosphonium clays of high ion exchange capacity, particularly of the montmorillonite type clays, highly depend on the number and carbon range of higher alkyl groups. Also, different types of phosphonium clays exhibit optimum gellant interactions in organic fluids of different polarity.

High monoalkyl phosphonium clays possess superior gellant properties in highly polar media, particularly when overtreated. Their optimum gellant interaction is in the $C_{20}$–$C_{22}$ carbon range of higher alkyl groups. Choice polar fluids are alkyd type polyesters, lubricant diesters, polyesters and polyphenyl ethers.

High dialkyl phosphonium clays are particularly outstanding gellants in media of relatively medium polarity such as aromatic hydrocarbons and unsaturated polyesters. Their optimum gellant properties are in the $C_{16}$–$C_{18}$ carbon range.

High trialkyl phosphonium clays show excellent gellant properties in both highly polar and nonpolar media if the number of carbon atoms per high alkyl groups is in the right range. Tri-$C_8$ and -$C_9$ derivatives exhibit excellent gellant interaction with alkyd resins while tri-$C_{14}$ to $C_{18}$ derivatives will gel paraffinic poly-α-olefin lubricants such as polydecene.

The unexpected gelling properties of the present tetraalkyl phosphonium clays in organic liquids can be utilized by using individual phosphonium clay compositions or mixtures thereof. Mixtures of phosphonium clays with other gelling agents such as ammonium clays and silica can be also used. Such mixtures are particularly advantageous for gelling complex systems such as paints.

Unexpectedly, tetraalkyl phosphonium clays substituted with polar groups such as hydroxy exhibit excellent gellant properties. While maintaining the gellant properties, which are often important, e.g. in the coatings application of organoclays, such substituted tetraalkyl phosphonium clays may interact with the substrate to be gelled. For example, the hydroxy substituent of phosphonium clays can react with the epoxide groups of epoxy resin systems.

Additionally, substituted tetraalkyl phosphonium clays often possess unique complexing properties. For example, tertiary phosphino and aminoalkyl phosphonium clays complex transition metal compounds, particularly compounds of Group VIII metals, via coordinative bonding between their trivalent phosphorus or nitrogen and the transition metal. Such complexes represent a unique group of transition metal complex catalysts, wherein the phosphine or amine ligand is anchored to the aluminosilicate via the ionically bound quaternary phosphonium group. Such layered clay catalysts having at least one high alkyl substituent are preferred because their ability to gel increases their effective surface.

EXAMPLES

General Procedures for the Preparation of Tetraalkyl Phosphonium Montmorillonite Clays (Examples 1, 3-11)

The procedures for the preparation of phosphonium montmorillonite clays take advantage of the ready dispersability of such hydrophylic clays in water and in water isopropanol mixtures. The composition of the medium is dependent on the solubility of the tetraalkyl phosphonium chloride salt clay reactant to be used. Usually it was attempted to prepare a 10% solution. If the salt was water soluble, water was used to disperse the clay reactant as well. If warm water did not dissolve the salt, isopropanol was added. Isopropanol-water mixtures were used, up to 50% isopropanol concentration as solvents for salts. Once a solution was made, a solvent medium of matching composition was made for dispersing the clay.

The salt solutions were added to the stirred clay suspensions of 1 to 3% concentration which were pre-warmed to 50° C. The temperature of the salt solution was ambient in cases of high solubilities. Salts of lower solubility were reacted as 45°-50° C. solutions as required. All the solution was added at once. This resulted in an instantaneous reaction. Nevertheless, stirring of the reaction mixture was continued to complete the reaction and to obtain a homogeneous solid product. The product was usually hydrophobic, large in particle size and ready to filter. Nevertheless, it retained a large (about ninefold) amount of water which was removed by drying in vacuo.

The phosphonium chloride reactants were usually employed in amounts corresponding to the ion exchange capacity of the clays. As a rule, complete ion exchange occurred and product analyses showed that the organic content of the clays was close to the calculated value. The chlorine contents were minimal, indicating that after reaction with sodium montmorillonite, the chloride anion of the phosphonium salt was removed as an aqueous sodium chloride filtrate.

One of the most characteristic properties of individual phosphonium clays is their X-ray spectrum. From the X-ray data, the repeat distances of the layered phosphonium clays can be calculated. These distances are recorded and discussed since they depend on the structure of the phosphonium moieties which are between the inorganic aluminosilicate layers.

phosphonium hectorite clay products were dried in vacuo at 0.1 mm at room temperature. The dry products were then analyzed for elemental composition and X-ray spectra.

As it is shown by Table I, the found composition of the modified clays is surprisingly close to the values calculated assuming the exchange of 100 miliequivalent metal for phosphonium per 100 g of clay. Also, in those cases wherein a 50% excess of the quaternary phosphonium salt reactant was used, the found composition rather well agreed with

TABLE I
INTERPLANAR SPACING OF 001 REFLECTION ($^d$001) AND COMPOSITION OF CLAYS MODIFIED WITH VARIOUS HIGHER MONO- AND TRIALKYL PHOSPHONIUM CHLORIDES

| Type | Seq. No. | Structure of Quaternary Chloride Clay Modifier 100 me$^{(a)}$ | Spacing $d$001 A | Calc'd. for 100$^{(b)}$(150$^d$)me C | H | P | Cl$^{(d)}$ | Found C | H | P | Cl |
|---|---|---|---|---|---|---|---|---|---|---|---|
| I | 1 | (No Modifier, Starting clay) | 12.6 | | | | | | | | 0.25 |
| II | 3 | [(CH$_3$)$_3$P$^+$C$_{12}$H$_{25}$]Cl$^-$ | 16.1 | 14.74 | 2.80 | 2.53 | — | 13.42 | 2.94 | 2.22 | 0.05 |
|  |  |  |  |  |  |  |  | 14.13 | 2.74 | 2.75 | 0.41 |
|  | 4 | [(C$_2$H$_5$)$_3$P$^+$C$_{12}$H$_{25}$]Cl$^-$ | 17.6 | 17.10 | 3.19 | 2.45 | — | 16.63 | 3.23 | 2.53 | 0.47 |
|  | 5 | [(C$_2$H$_5$)$_3$P$^+$C$_{18}$H$_{37}$]Cl$^-$ | 22.4 | 21.37 | 3.14 | 2.30 | — | 22.10 | 4.05 | 2.41 | 0.79 |
|  | 6 | same as above but 150 me$^{(c)}$ | 23.0 | 27.86 | 4.09 | 2.99 | 1.14 | 28.25 | 4.86 | 3.27 | 1.30 |
|  | 7 | [(C$_4$H$_9$)$_3$P$^+$C$_{18}$H$_{37}$]Cl$^-$ | 23.0 | 26.48 | 4.74 | 2.28 | — | 26.09 | 4.72 | 2.46 | 0.63 |
| III | 10 | [(C$_8$H$_{17}$)$_3$P$^+$CH$_3$]Cl$^-$ | 23.2 | 22.05 | 3.96 | 2.27 | — | 24.83 | 4.34 | 2.76 | 0.45 |
|  | 11 | [(C$_{16}$H$_{33}$)$_3$P$^+$CH$_3$]Cl$^-$ | 30.5–31.5 | 34.63 | 6.04 | 1.82 | — | 32.64 | 5.62 | 2.05 | 0.67 |
|  | 12 | same as above, but 150 me$^c$ | 32.5 | 42.47 | 7.42 | 2.23 | 0.85 | 38.82 | 7.20 | 2.34 | 1.18 |
|  | 13 | [(C$_8$H$_{17}$)$_3$P$^+$C$_2$H$_5$]Cl$^-$ | 21.0 | 22.68 | 4.10 | 2.25 | — | 21.81 | 4.09 | 2.24 | 0.20 |
|  | 14 | same as above, but 150 me$^c$ | 22.6 | 29.38 | 5.31 | 2.92 | 1.11 | 25.35 | 4.90 | 2.75 | 0.49 |

$^{(a)}$Stoichiometric amount of quaternary was used assuming 100 miliequivalent cation exchange capacity for 100 g of clay
$^{(b)}$Composition calculated assuming complete ion exchange,
$^{(c)}$Stoichiometric amount of quaternary was used assuming 150 miliequivalent cation exchange capacity for 100 g of clay.
$^{(d)}$Composition calculated assuming 100 me phosphonium exchange plus 50 me phosphonium halide absorption.

EXAMPLE 1 — Preparation of Tetraalkyl Phosphonium Hectorites

The starting clay was a refined sodium hectorite supplied by N. L. Industries. Its composition can be expressed by the following summary formula:

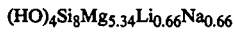

(HO)$_4$Si$_8$Mg$_{5.34}$Li$_{0.66}$Na$_{0.66}$

This clay was indicated to have an exchangeable ion capacity of 100 milliequivalents per 100 g dry material. Accordingly, 0.1 mole of phosphonium chloride per 100 g clay was used to effect the exchange of the inorganic cations of the clay for the organic phosphonium cations.

The products derived from the reaction of a number of higher monoalkyl and trialkyl phosphonium chlorides are shown in Table I.

The higher monalkyl phosphonium chlorides could be dissolved in water to form 5% solutions which were then added dropwise to a well stirred 2% aqueous suspension of the clay at room temperature. Flocculation of large clay aggregates started immediately and stirring became difficult during the first part of the addtion. By the time the addition was complete, the mixture was easy to stir. After an hour mixing, the mixture was filtered readily by suction and washed by distilled water.

Among the first higher trialkyl phosphonium chlorides, only the first one was water soluble. The others were dissolved in a 1 to 1 mixture of water and isopropanol and in these cases a similar solvent mixture was used to suspend the hectorite starting clay. In the case of the methyl trihexadecyl phosphonium chloride, it was also necessary to use a higher temperature of 70° C. to effect solution. In that case, the reaction was also carried out at the elevated temperature. The tetraalkyl the one calculated assuming a complete complexing of the excess phosphonium salt. There is no apparent difficulty of ion exchange for the butyl higher trialkyl phosphonium salts.

Table I also shows some X-ray data, i.e., the interplanar spacings of the 001 reflection. These spacings indicate the interlayer repeat distances. The products were examined by powder X-ray diffraction using a Norelco goniometer with Cu radiation. All of the derivatives showed the characteristic diffraction pattern of a clay that had been intercalated. The specific features of the X-ray pattern were: generally broadened peaks, a series of three to four hk0 line which did not shift with the different intercalates, and the 001 reflection. The interplanar spacing of the 001 reflection ($^d$001) is dependent on the amount, geometry and orientation of the intercalating species. The unmodified clay has $^d$001-12.6 Å while the modified clays have $^d$001 ranging from 15.5 Å to 32.5 Å. Some samples are more crystalline than others. This is indicated by a range of values for $^d$001. It should also be noted that the samples that were treated with an excess of salt gave a sharper X-ray pattern than those treated with a stoichiometric amount of salt. This may be due to an incomplete coverage of the clay surface in the absence of excess quaternary reactant.

In the case of both the higher monoalkyl (Type II) and higher trialkyl (Type III) phosphonium clays, the interplanar spacing increased with the increased number of carbons per long alkyl group. However, for a comparable number of carbon atoms per chain, the higher trialkyl phosphonium clays had a much larger spacing.

EXAMPLE 2 — Thermal Stability of Quaternary Tetraalkyl Phosphonium Hectorites The thermal stability of some of the phosphonium hectorites of Example 1 was studied under nitrogen. The rate of weight loss of samples was examined between 0 and 900° C. at a heating rate of 6° C. per minute. Methyl trioctyl ammonium hectorite was similarly prepared and tested for comparison. The results are shown in Table II.

The data show that methyl trioctyl phosphonium hectorite is thermally much more stable than its nitrogen analog (Seq. No. 2 vs. 1) It is also shown that the decomposition of the octadecyl triethyl phosphonium hectorite starts at a higher temperature than that of the methyl higher trialkylphosphonium hectorites (Seq. No. 4 vs. 2 and 3). In contrast, changing the length of higher alkyl chains of the methyl trioctyl phosphonium derivative has no significant effect on the thermal stability (Seq. No. 2 vs 3).

in water to yield stable suspensions which can be easily and effectively stirred. Its interplanar repeat distance is 12 Å.

In the present example, two higher alkyl trimethyl phosphonium chlorides and four higher alkyl triethyl phosphonium chlorides were reacted with the above-described sodium montmorillonite to yield the corresponding phosphonium montmorillonites as shown by Table III.

TABLE III

PREPARATION, INTERPLANAR SPACING AND COMPOSITION OF HIGHER MONO-ALKYL TRIMETHYL AND TRIETHYL PHOSPHONIUM DERIVATIVES OF MONTMORILLONITE (MINERAL COLLOID BP)
$\{[CH_3(CH_2)_{0-1}]_2P^+ C_mH_{2n+1}\}$ Clay$^-$ ; m = 11-20

| Seq. No. | Structure of Quaternary Cation on Clay | Chloride Reactant Used Moles | Reaction Medium | X-ray Spacing $d_{001}$, A | %, Elemental Composition of Modified Clay | | | | | | |
|---|---|---|---|---|---|---|---|---|---|---|---|
| | | | | | Calcd. for 99 me 100g. Dry Clay | | | Found | | | |
| | | | | | C | H | P | C | H | P | Cl |
| 1 | $[(CH_3)_3P^+C_{11}H_{23}]$ | 0.018$^{(a)}$ | $H_2O$ | | 13.80 | 2.65 | 2.54 | 13.42 | 2.94 | 2.22 | 0.05 |
| 2 | $[(CH_3)_3P^+C_{14}H_{29}]$ | 0.0097$^{(a)}$ | $H_2O$ | 18.4 | 16.20 | 3.04 | 2.46 | 17.20 | 3.45 | — | 0.16 |
| 3 | $[(CH_3)_3P^+C_{20}H_{41}]$ | 0.023$^{(b)}$ | IPA-$H_2O^{(d)}$ | 20.8 | 20.54 | 3.75 | 2.30 | 20.64 | 4.14 | 2.35 | 0.13 |
| 4 | $[(C_2H_5)_3P^+C_{12}H_{25}]$ | 0.027$^{(a)}$ | $H_2O$ | 17.8 | 16.96 | 3.16 | 2.43 | 16.16 | 3.24 | 2.33 | 0.05 |
| 5 | $[(C_2H_5)_3P^+C_{16}H_{33}]$ | 0.027$^{(a)}$ | $H_2O$ | 21.0 | 19.86 | 3.64 | 2.33 | 19.48 | 3.91 | 2.25 | 0.10 |
| 6 | $[(C_2H_5)_3P^+C_{18}H_{37}]$ | 0.027$^{(a)}$ | $H_2O$ | 22.1 | 21.22 | 3.86 | 2.28 | 22.23 | 4.24 | 2.26 | 0.22 |
| 7 | $[(C_2H_5)_3P^+C_{20}H_{41}]$ | 0.023$^{(c)}$ | IPA-$H_2O^{(d)}$ | 21.8 | 22.50 | 4.07 | 2.24 | 23.52 | 4.76 | 1.98 | 0.19 |

$^{(a)}$About 10% water solution at 50° C.
$^{(b)}$About 3.4% in 1 to 4 ispropanol-water at 50° C.
$^{(c)}$About 10% is 1 to 4 isopropanol-water.
$^{(d)}$Isopropanol-water in a ratio of 1 to 4.

In all these reactions, a stable suspension of the sodium montmorillonite in distilled water or isopropanol-water was used. The clay concentration was set at about 2% in the reaction mixture. The majority of the phosphonium chloride reactants was dissolved in warm water to provide reactant solutions of approximately 10% concentration at 50° C. In cases of salts having low water solubility, a warm 1 to 4 mixture of isopropanol and water was used as a solvent. These latter solutions were reacted with clays suspended in solvent mixtures of identical composition.

TABLE II

THERMOGRAVIMETRIC ANALYSIS$^a$ OF QUATERNARY PHOSPHONIUM AND AMMONIUM DERIVATIVES OF REFINED HECTORITE CLAYS

| Sequence No. | Chemical Structure of Quaternary Group | Decomposition Temp., °C | | | Total Weight Loss, % | Analysis: Sum of C,H and N or P, % |
|---|---|---|---|---|---|---|
| | | Onset | Max. Rate | End | | |
| 1 | $(C_8H_{17})_3N^+CH_3$ | 325 | 405 | 475 | 25 | 29.2 |
| 2 | $(C_8H_{17})_3P^+CH_3$ | 365 | 480 | 545 | 33 | 28.3 |
| 3 | $(C_{16}H_{33})_3P^+CH_3$ | 310$^b$ | 510 | 545 | 39 | 40.3 |
| 4 | $C_{18}H_{37}P^+(C_2H_5)_3$ | 435 | 505 | 575 | 28 | 28.6 |

$^a$Rate of Heating: 6° C per minute, S. S. Planchet, Range: 0–900° C, $N_2$flow 350 ml per min.
$^b$The main decomposition reaction starts at a higher temperature.

EXAMPLE 3 — Preparation of Higher Monoalkyl Trimethyl and Triethyl Phosphonium Montmorillonites The starting clay was a refined sodium montmorillonite supplied by the Georgia Kaolin Company which is available under the trade name Mineral Colloid BP. This clay is prepared from Penfield, Wyoming montmorillonite. The product has a water content of about 10%. Its composition corresponds to the following summary formula:

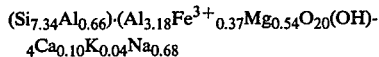
$(Si_{7.34}Al_{0.66})\cdot(Al_{3.18}Fe^{3+}{}_{0.37}Mg_{0.54}O_{20}(OH)$-
$4Ca_{0.10}K_{0.04}Na_{0.68}$ This clay was indicated to have an ion exchange capacity of 90 miliequivalents per 100 g dry clay. In the present work, however, it was found that it has a minimum ion exchange capacity of 99 me per 100 g towards tetraalkyl phosphonium chlorides having at least one higher alkyl group. Up to 5% this clay can be easily dispersed All the reactants were carried out at 50° C., by adding 99 me of the phosphonium chloride solution to the well stirred clay suspension at once. A sudden large increase of viscosity occurred immediately. In about 2–3 minutes, the viscosity became manageable. After 30 minutes stirring the mixture was filtered with suction and the cake was washed with distilled water on the filter funnel. In case of the isopropanol-water mixtures, the identical solvent mixture was used for washing at first. This was then followed by water. The washing liquids were employed in three equal volume portions. At the 30 g starting clay level this volume was 300 ml. The washed, filtered products still had about 90% water content. They were dried under 0.1 mm pressure, either at room temperature or at 60° C. The dry products were ball milled overnight and then passed through a 200 mesh screen. Thereafter, they were analyzed and evaluated.

The found carbon, hydrogen and phosphorus content of the products was in general close to the calculated values (Table III). The chlorine content was 0.22% or less, indicating that a true ion exchange reaction rather than adduct complex formation took place. The formation of the clay derivatives resulted in greatly increased interplanar distances. These distances are directly proportional to the number of carbons in the higher n-alkyl group of the phosphonium clay substituent. In the range icant change from the $C_{12}$ to $C_{16}$ alkyl group. Also in the case of the n-$C_{16}$ alkyl group, the interplanar distance was virtually the same for the tri-n-butyl and the tri-i-butyl derivatives Seq. No's. In the case of the n-$C_{12}$ alkyl compounds, the tri-n-butyl phosphonium clay had a smaller interplanar distance than the tri-i-butyl derivative.

TABLE IV

INTERPLANAR SPACING OF 001 REFLECTION AND COMPOSITION OF HIGHER MONOALKYL TRI-n-BUTYL AND TRI-i-BUTYL PHOSPHONIUM DERIVATIVES OF MONTMORILLONITE (MINERAL COLLOID BP)

$[(C_4H_9)_4P^+C_mH_{2m+1}]$ Clay$^-$; m = 12–18

| Seq. No. | Structure of Quaternary Cation on Clay | Chloride Reactant Used, Moles | Reaction Temp. °C | X-Ray Spacing $d_{001}$, A | Elemental Composition of Modified Clay, % | | | | | | |
|---|---|---|---|---|---|---|---|---|---|---|---|
| | | | | | Calcd. for 99 me/ 100 g. Dry Clay | | | Found | | | |
| | | | | | C | H | P | C | H | P | Cl |
| 1 | $[(n-C_4H_9)_3P^+C_{12}H_{25}]$ | 0.027$^a$ | Ambient | 20.5 | 21.22 | 3.93 | 2.28 | 19.61 | 3.99 | 2.12 | 0.07 |
| 2 | $[(n-C_4H_9)_3P^+C_{16}H_{33}]$ | 0.022$^b$ | Ambient | 22.2–22.5 | 23.78 | 4.28 | 2.19 | 24.86 | 4.77 | 2.41 | 0.24 |
| 3 | $[(i-C_4H_9)_3P^+C_{12}H_{25}]$ | 0.024$^c$ | 45 | 22.5 | 21.22 | 3.86 | 2.28 | 21.71 | 4.27 | 2.20 | 0.11 |
| 4 | $[(i-C_4H_9)_3P^+C_{14}H_{29}]$ | 0.027$^c$ | 45 | 22.3 | 22.52 | 4.07 | 2.23 | 22.62 | 4.38 | 2.33 | 0.12 |
| 5 | $[(i-C_4C_9)_3P^+C_{16}H_{33}]$ | 0.027$^c$ | 45 | 22.4 | 23.05 | 4.26 | 2.19 | 23.85 | 4.52 | 2.16 | 0.08 |
| 6 | $[(i-C_4H_9)_3P^+C_{18}H_{37}]$ | 0.135$^a$ | Ambient | 23.0 | 24.97 | 4.47 | 2.16 | 25.22 | 4.90 | 2.09 | 0.14 |

$^a$About 10% water solution.
$^b$About 15% water solution containing 10% mole excess quaternary due to impure quaternary.
$^c$About 10% water solution at 45° C.

examined, the increase per two additional carbon atoms is in the order of 1 Å. However, this increase is not always the same, it is more of an average value. Dependent on their inorganic structure, layered clays seem to prefer to assume structures having certain discrete values. The n-alkyl group being equal ($C_{20}$), a triethyl phosphonium derivative had an interplanar distance one Å greater than a trimethyl phosphonium group. (Seq. No. 7 vs 3).

EXAMPLE 4 — Preparation of Higher Monoalkyl Tributyl Phosphonium Montmorillonites Higher monoalkyl tri-n-butyl and tri-primary-i-butyl phosphonium chlorides were reacted with the Mineral Colloid BP clay of the previous example under similar conditions. A summary of the results is provided in Table IV.

The clay starting material was employed as a 2% aqueous suspension. This was possible since all the phosphonium chlorides of the present series were soluble in water. About 10% aqueous chloride solutions were used at either ambient temperatures or at about 45° C. All the phosphonium chlorides were again employed at the 99 me per 100 g dry clay treatment level. In the one case, wherein the quaternary salt was impure, a correspondingly larger quantity was used. The reaction process and the isolation of the products were basically the same as in the previous example.

As it is shown by Table IV, the found elemental composition of the clays was in fair agreement with the calculated values. It is felt that differences between the found and calculated values is mostly due to the impurities in the phosphonium chlorides of the present chlorides. These chlorides are viscous liquids very difficult to purify. The chlorine content of the products was again low indicating an essentially complete ion exchange.

The interplanar spacing was again directly proportional to the length of the higher alkyl chain as in the previous example. However, in the case of the higher alkyl triisobutyl phosphonium clays there was no signif- EXAMPLE 5 — Preparation of Docosyl Tri-$C_{1-4}$-Alkyl Phosphonium Montmorillonites Decosyl lower trialkyl phosphonium chlorides were reacted with the refined sodium montmorillonite of the previous example under similar conditions. A summary of the results is provided in Table V.

The clay starting material was again employed at a concentration to give a 2% suspension after the addition of the chloride solution. However, the docosyl trialkyl phosphonium chloride starting reactants of this example, in general, showed a lower water solubility than those previously used. Consequently, in this example, both the chlorides and the clay were dissolved inisopropanol-water mixtures.

On the addition of the chloride solutions to the clay suspensions, the same immediate reaction took place which was described in the previous example. The products were also isolated in a manner basically the same as was used previously.

The found elemental composition of the clays was again close to the theoretical calculated on the basis of assuming the reaction of all the phosphonium chloride, i.e., 99 me per 100 g dry clay. However, it is noted that all the found values are slightly higher in contrast to the more unevenly scattered values of the previous example. It is also interesting to observe that the chlorine contents found were smaller in this series than in the earlier.

The interplanar repeat distances of the docosyl trialkyl phosphonium clays indicate the direct effect of the increasing number of carbon atoms in the n-trialkyl part of the phosphonium moiety on the interplanar distance. From methyl to n-butyl the increase of this distance per carbon is increasing. It is interesting to observe that the interplanar distance of the tri-isopropyl phosphonium derivative is greatly increased over that of the corresponding tri-n-propyl compound (Seq. Nos. 3 vs 4). Branching of a small alkyl group apparently increases its effect on the interplanar distance.

TABLE V

INTERPLANAR SPACING OF 001 REFLECTION AND COMPOSITION OF DOCOSYL TRI-$C_{1-4}$-ALKYL PHOSPHONIUM DERIVATIVES OF MONTMORILLONITE (MINERAL COLLOID BP)

$[(C_nH_{2n+1})_3P^+C_{22}H_{45}]$ Clay$^-$; n = 1-4

| Seq. No. | R Group in Quaternary Cation $C_{22}H_{45}P^+R_3$ | Chloride Reactant Used, Moles | Reaction Medium | X-Ray Spacing $d_{001}$ A | Calcd for 99 me C | H | P | Found C | H | P | Cl(Br) |
|---|---|---|---|---|---|---|---|---|---|---|---|
| 1 | $CH_3$ | 0.010$^{(a)}$ | IPA/H$_2$O$^{(d)}$ | 22.4 | 21.87 | 3.96 | 2.25 | 22.29 | 4.34 | 2.24 | <0.0% |
| 2 | $C_2H_5$ | 0.045$^{(b)}$ | IPA/H$_2$O$^{(e)}$ | 23.0 | 23.77 | 4.27 | 2.19 | 23.80 | 4.51 | 2.20 | 0.10 |
| 3 | n-$C_3H_7$ | 0.018$^{(c)}$ | IPA/H$_2$O$^{(f)}$ | 24.2 | 25.56 | 4.57 | 2.13 | 26.24 | 4.93 | 2.34 | <0.05 |
| 4 | i-$C_3H_7$ | 0.018$^{(c)}$ | IPA/H$_2$O$^{(f)}$ | 25.7 | 25.56 | 4.57 | 2.13 | 26.42 | 5.01 | 2.23 | <0.03 |
| 5 | n-$C_4H_9$ | 0.018$^{(c)}$ | IPA/H$_2$O$^{(f)}$ | 26.0 | 27.24 | 4.85 | 2.07 | 28.05 | 5.18 | 2.29 | <0.03 |
| 6 | i-$C_4H_9$ | 0.135$^{(a,g)}$ | IPA/H$_2$O$^{(d)}$ |  | 27.24 | 4.85 | 2.07 | 26.67 | 5.05 | 2.02 | (0.63) |

Miliequivalent quaternary per 100 g starting dry clay.

$^{(a)}$About 2.7% in 1 to 3 isopropanol-water at 53° C.
$^{(b)}$About 6% in about 1 to 4 isopropanol-water.
$^{(c)}$About 10% in 1 to 5 isopropanol-water.
$^{(d)}$Isopropanol-water in a ratio of 1 to 3.
$^{(e)}$Isopropanol-water in a ratio of 1 to 4.
$^{(f)}$Isopropanol-water in a ratio of 1 to 5.
$^{(g)}$Quaternary bromide reactant was used.

EXAMPLE 6 — Preparation of Higher Dialkyl Dimethyl and Diethyl Phosphonium Montmorillonites Higher dialkyl dimethyl and diethyl phosphonium chlorides were reacted with the sodium montmorillonite of the previous example in the usual manner. The results are summarized in Table VI.

The clay starting material was again used at the 2% concentration level. The solvent media, i.e., water or isopropanolic water were identical for the clay and the phosphonium chloride reactants. The phosphonium chloride solution of 10 to 37% concentration was added all at once to the 2% clay suspension at 50° C. The treatment level was 99 me chloride per 100 g vacuum dried clay. On the addition of the chloride an immediate reaction occurred in the usual manner. For the isolation of the higher dialkyl dimethyl and diethyl phosphonium montmorillonite products basically the previously used procedure was employed.

As it is shown by the analytical data of Table VI, the found elemental composition of the products is in good agreement with their calculated values. It is noted that the three higher dialkyl dimethyl montmorillonites had only trace amounts of chlorine. This indicates that there was no excess, unconverted phosphonium chloride reactant but an essentially complete ion exchange.

The interplanar spacing of the quaternary higher dialkyl phosphonium clays of Table VI is in general much larger than that of the quaternary higher monoalkyl phosphonium clays in Table III. For example, the spacing of dioctadecyl diethyl phosphonium montmorillonite of Table VI, Seq. No. 4 is 28.4° A while that of the monooctadecyl triethyl phosphonium montmorillonite of Table III, Seq. No. 5 is 22.1° A. Within the higher dialkyl series of Table VI, the spacing is generally directly proprotional to the length of the alkyl chains. However, there is no increase in spacing from the dioctyl to the didecyl derivative (Seq. Nos. 1,2).

TABLE VI

PREPARATION INTERPLANAR SPACING AND COMPOSITION OF HIGHER DIALKYL DIMETHYL AND DIETHYL PHOSPHONIUM DERIVATIVES OF MONTMORILLONITE (MINERAL COLLOID BP)

$[(C_rH_{2r+1})_2 P^+(CH_2)_{0-1}CH_3]$ Clay$^-$; r = 8-18

| Seq. No. | Structure of Quaternary Cation on Clay | Chloride Reactant Used, Moles | Reaction Medium | X-Ray Spacing $d_{001}$, A | Calc for 99 me/ 100 g Dry Clay C | H | P | Found C | H | P | Cl |
|---|---|---|---|---|---|---|---|---|---|---|---|
| 1 | $[(CH_3)_2P^+(C_8H_{17})_2]$ | 0.020$^{(a)}$ | H$_2$O | 20.5 | 16.96 | 3.16 | 2.43 | 20.38 | 4.12 | 2.53 | 0.02 |
| 2 | $[(CH_3)_2P^+(C_{10}H_{21})_2]$ | 0.020$^{(b)}$ | IPA/H$_2$O$^{(e)}$ | 20.3 | 19.86 | 3.64 | 2.33 | 20.28 | 4.02 | 2.51 | 0.02 |
| 3 | $[(CH_3)_2P^+(C_{12}H_{25})_2]$ | 0.027$^{(c)}$ | IPA/H$_2$O$^{(f)}$ | 22.6–23.4 | 22.52 | 4.07 | 2.22 | 21.53 | 4.30 | 2.13 | Nil |
| 4 | $[(C_2H_5)_2P^+(C_{18}H_{37})_2]$ | 0.014$^{(d)}$ | IPA/H$_2$O$^{(g)}$ | 28.4* | 30.35 | 5.35 | 1.96 | 30.40 | 5.88 | 2.00 | 0.17 |

$^{(a)}$About 10% water solution at room temperature.
$^{(b)}$About 10% at ambient temperature.
$^{(c)}$About 37% at ambient temperature.
$^{(d)}$About 18% at 70° C.
$^{(e)}$Isopropanol-water in ratio of 1 to 3.
$^{(f)}$About 2.3% isopropanol in water.
$^{(g)}$Isopropanol-water in a ratio of 1 to 4.

EXAMPLE 7 — Preparation of Quaternary Higher Trialkyl Phosphonium Montmorillonites To a well stirred, stable 2% clay suspension, containing 30 g. of Mineral Colloid BP of 10% water content from Georgia Kaolin Co., in a water-isopropanol medium at 50° C., 99 miliequivalent per 100 g. dry clay (i.e., 0.027 mole) of quaternary chloride dissolved in an identical waterisopropanol medium (9% quaternary chloride) at approximately 45–50° C. was added all at once. The isopropanol in water concentration was kept at the minimum required to prepare approximately 9% solutions of the quaternary chlorides at 45–50° C. This concentration was 20% in the preparation of clays having Sequence Numbers 1 and 3, 33% for Seq. Nos. 2, 4, 5 and 9 and 50% for Seq. Nos. 6 and 7 in Table VII. In general, as the carbon number of the higher alkyl groups increased, the concentration of the isopropanol had to be increased as well. In the case of the trihexadecyl phosphonium chlorides of Table VIII (Seq. Nos. 3 and 4,) a one to one mixture of isopropanol and water was used.

TABLE VII

INTERPLANAR SPACING OF 001 REFLECTION AND COMPOSITION OF QUATERNARY TRIHEXYL, TRIOCTYL AND TRIDECYL PHOSPHONIUM DERIVATIVES OF MONTMORILLONITE CLAY (MINERAL COLLOID BP)

| Seq. No. | Structure of Quaternary Cation on Clay | Chloride Reactant Used, Moles | Reaction Medium | X-Ray Spacing $d_{001}$, A | Calc for 99 me/ 100 g Dry Clay | | | Found | | | |
|---|---|---|---|---|---|---|---|---|---|---|---|
| | | | | | C | H | P | C | H | P | Cl |
| 1 | $[(C_6H_{13})_3P^+CH_3]$ | $0.027^{(a)}$ | IPA/H$_2$O$^{(e)}$ | 17.8 | 17.71 | 3.29 | 2.40 | 17.63 | 3.60 | 2.25 | 0.04 |
| 2 | $[(C_8H_{17})_3P^+CH_3]$ | $0.027^{(b)}$ | IPA/H$_2$O$^{(f)}$ | 22.1–22.6 | 21.88 | 3.97 | 2.26 | 21.63 | 4.35 | 2.28 | 0.08 |
| 3 | $[(C_8H_{17})_3P^+C_2H_5]$ | $0.027^{(a)}$ | IPA/H$_2$O$^{(e)}$ | 22.2 | 22.52 | 4.01 | 2.23 | 22.61 | 4.48 | 2.24 | 0.13 |
| 4 | $[(C_8H_{17})_3P^+n-C_3H_7]$ | $0.027^{(b)}$ | IPA/H$_2$O$^{(f)}$ | 22.0 | 23.15 | 4.18 | 2.21 | 23.21 | 4.60 | 2.27 | 0.01 |
| 5 | $[(C_8H_{17})_3P^+n-C_4H_9]$ | $0.027^{(b)}$ | IPA/H$_2$O$^{(f)}$ | 22.5 | 23.77 | 4.28 | 2.19 | 23.93 | 4.67 | 2.18 | 0.09 |
| 6 | $[(C_8H_{17})_3P^+n-C_5H_{11}]$ | $0.027^{(c)}$ | IPA/H$_2$O$^{(g)}$ | 22.6 | 24.37 | 4.38 | 2.17 | 20.75 | 4.20 | 1.93 | 0.02 |
| 7 | $[(C_8H_{17})_3P^+n-C_6H_{13}]$ | $0.027^{(c)}$ | IPA/H$_2$O$^{(g)}$ | 22.4 | 24.97 | 4.47 | 2.15 | 20.46 | 4.16 | 1.78 | 0.04 |
| 8 | $[(C_8H_{17})_3P^+CH_2\text{—}\langle O\rangle]$ | $0.027^{(c)}$ | IPA/H$_2$O$^{(g)}$ | 22.4 | 25.70 | 4.04 | 2.14 | 23.16 | 4.10 | 1.76 | 0.06 |
| 9 | $[(C_{10}H_{21})_3P^+CH_3]$ | $0.027^{(d)}$ | IPA/H$_2$O$^{(g)}$ | 25.2 | 25.56 | 4.57 | 2.13 | 25.79 | 4.99 | 2.09 | 0.06 |

(a) About 10% solution at 40° C.
(b) About 9% at 50° C.
(c) About 10% solution at 50° C.
(d) About 6% solution at 50° C.
(e) Isopropanol-water at 1 to 5 ratio
(f) Isopropanol-water at 1 to 3 ratio
(g) Isopropanol-water at 1 to 2 ratio

TABLE VIII

INTERPLANAR SPACING OF 001 REFLECTION AND COMPOSITION OF QUATERNARY TRINONYL AND TRIHEXADECYL PHOSPHONIUM DERIVATIVES OF MONTMORILLONITE CLAY (MINERAL COLLOID BP)

| Seq. No. | Structure of Quaternary Cation on Clay | Chloride Reactant Used, Moles | i-Propanol Water Ratio$^c$ | X-ray Spacing 001 A | Calc for 99 me/ 100 g dry clay | | | Found | | | |
|---|---|---|---|---|---|---|---|---|---|---|---|
| | | | | | C | H | P | C | H | P | Cl |
| 1 | $(C_9H_{19})_3P^+CH_3$ | $0.0180^a$ | 1/3 | | 23.77 | 4.28 | 2.19 | 23.91 | 4.70 | 2.21 | 0.09 |
| 2 | $(C_9H_{19})_3P^+C_2H_5$ | $0.0135^a$ | 1/4 | 23.5 | 24.37 | 4.38 | 2.17 | 24.45 | 4.83 | 2.38 | 0.11 |
| 3 | $(C_{16}H_{33})_3P^+C_2H_5$ | $0.0300^b$ | 1/1 | 31.5 | 34.84 | 6.08 | 1.79 | 35.95 | 6.57 | 2.19 | 0.24 |
| 4 | $(C_{16}H_{33})_3P^+CH_2CH(CH_3)_2$ | $0.2700^b$ | 1/1 | 34.4 | 35.65 | 6.21 | 1.76 | 35.92 | 6.42 | 1.82 | 0.08 |

$^a$About 10% solution at 40°.
$^b$About 5% solution at 40°.
$^c$The concentration of the clay reactant in the final isopropanol-water medium is about 2%.

Upon mixing the reactants, a large temporary increase of the reaction mixture viscosity was observed, followed by a gradual breakdown of this increased viscosity. The reaction mixture was stirred at 50° C. for 30 minutes and then immediately filtered with suction. The filter-cake was washed two times with ten-fold quantities of the isopropanolwater mixture used as the reaction medium and once with a similar quantity of distilled water. Thereafter, the product was dried in vacuo (0.1 mm) at 60° C. and ball-milled for 18 hours. The ball-milled product was submitted for X-ray and elemental analysis; it was then sieved through a 200 mesh screen and subjected to testing.

The found elemental compositions of the phosphonium clay products are in excellent agreement with the calculated values in all cases but two (Seq. Nos. 6 and 7). Particularly encouraging are the low chlorine values which are indicative of complete ion exchange at the relatively high 99 milliequivalent quaternary chloride per 100 g clay treatment level. The low phosphonium contents reported for both the pentyl and hexyl trioctyl phosphonium clay products (Seq. Nos. 6 and 7) have been substantiated and are probably due to a low quaternary content of the starting chlorides.

The interplanar spacings of the quaternary higher trialkyl methyl phosphonium clays of Table VII is much higher than those of the corresponding higher dialkyl analogs of Table VI. For example, the spacings of the trioctyl and tridecyl clays of Table VII, Seq. Nos. 2 and 10, were much larger than those of the dioctyl and didecyl clays of Table VI, Seq. Nos. 1 and 2.

It is interesting that the interplanar spacing of all the quaternary trioctyl phosphonium clays from the methyl through the hexyl derivative (Seq. Nos. 2–7) is essentially the same (22.0–22.6 Å). Even, the benzyl trioctyl phosphonium clay has a similar spacing (Seq. No. 8). In contrast, decreasing the lengths of the higher trialkyl substituents from eight carbons to six carbons results in a largely decreased spacing (4.5 Å, Seq. No. 1 vs 2). Increasing the length of the trialkyl group from eight carbons to ten carbons also results in a substantially increased spacing (2.9 Å, Seq. No. 2 vs 9). However, it is noted that this increase is down to almost half the value observed for the analogous 2 carbon change from the trihexyl to the trioctyl group.

The above data on the interplanar spacing of quaternary higher trialkyl phosphonium montmorillonites can be explained by assuming a perpendicular orientation of the higher alkyl groups relative to the surface of the aluminosilicate layers.

The data indicate that a definite perpendicular orientation of the three higher n-alkyl groups relative to the surface of the aluminosilicate layers does not occur until their carbon number is above 6 per chain. Furthermore, it seems that the accommodation of the fourth alkyl group of these quaternary derivatives in the $C_1$ to $C_6$ range without affecting the interplanar spacing is best explained by an orientation parallel to the plane. For example, in the case of the hexyl trioctyl phosphonium montmorillonite FIG. 1 indicates the proposed orientation.

The interplanar spacings of the two quaternary trihexadecyl phosphonium clays of Table III are unexpectedly low and different. The low values can be explained, however, if a non-perpendicular orientation of the hexadecyl groups is assumed. The significant difference between the interplanar spacings of the ethyl and isobutyl trihexadecyl phosphonium clays can be apparently attributed to alkyl branching. The branches of the isobutyl substituent leads to a considerable increase of interplanar spacing because it is not oriented parallel to the surface of the aluminosilicate surface.

This hypothesis also explains the adverse effect of increasing the number of carbons of the fourth alkyl group on the gelling ability of such clays as described in Example 23.

EXAMPLE 8 — Preparation of Unsymmetrically Substituted Higher Monoalkyl Phosphonium Montmorillonites According to the general procedure described in the previous example, the unsymmetricaal low trialkyl substituted high monoalkyl phosphonium montmorillonites of Table IX were prepared. Most of the preparations were carried out in water media, since the corresponding phosphonium chloride starting materials were sufficiently water soluble. One of the phoshoium salts had a higher alkyl substituent with varying even number of carbon atoms in the 24 to 28 range. As it is indicated by the formula of the quaternary cation, the average number of carbon atoms was 27 (Seq. No. 2).

EXAMPLE 9 — Preparation of Unsymmetrically Substituted Higher Dialkyl Phosphonium Montmorillonites To a stirred 2% suspension of 30 g of the sodium montmorillonite in a one to five mixture of isopropanol and water, 0.027 mole of the appropriate phosphonium chloride was added as a 10% solution in a solvent mixture of the same composition. As usual, both the clay suspension and the phosphonium salt were at about 50° C. when mixed. An instantaneous reaction occurred in the usual manner. The products were isolated following the general procedure of the previous examples. The analyses of the dry products indicated that the expected phosphonium substitution of the clay occurred as shown by Table X.

TABLE X

QUATERNARY UNSYMMETRICALLY SUBSTITUTED LOW DIALKYL HIGH DIALKYL PHOSPHONIUM DERIVATIVES OF MONTMORILLONITE CLAY (MINERAL COLLOID BP)

| | | Elemental Composition of Modified Clay, % | | | | | | |
|---|---|---|---|---|---|---|---|---|
| Seq. No. | Structure of Quaternary Cation on Clay | Calcd. for 100 me/ 100 g Dry Clay | | | Found | | | |
| | | C | H | P | C | H | P | Cl |
| 1 | $(C_{12}H_{25})_{12}P^+(C_2H_5)i$-$C_4H_9$ | 24.97 | 4.47 | 2.15 | 26.14 | 5.10 | 2.31 | 0.09 |
| 2 | $(C_{16}H_{33})_2P^+(C_2H_5)i$-$C_4H_9$ | 25.59 | 4.43 | 2.13 | 26.51 | 4.91 | 2.20 | 0.25 |
| 3 | $(C_{12}H_{25})_2P^+(CH_2CH=CH_2)i$-$C_4H_9$ | 29.35 | 5.19 | 1.99 | 30.29 | 5.77 | 1.91 | 0.11 |

EXAMPLE 11 — Preparation of Vinylbenzyl Triethyl Phosphonium Montmorillonite 45 g montmorillonite clay is dispersed in a 2 to 1 mixture of water-isopropanol at 45° C. to yield a 3% suspension. To the well stirred suspension, a 15% solution of 13.55 g (0.05 mole) of vinylbenzyl triethyl phosphonium chloride is added at 45° C. at once. This re-

TABLE IX

INTERPLANAR SPACING OF 001 REFLECTION AND COMPOSITION Of QUATERNARY UNSYMMETRICALLY SUBSTITUTED LOW TRIALKYL HIGH MONOALKYL PHOSPHONIUM DERIVATIVES OF MONTMORILLONITE CLAY (MINERAL COLLOID BP)

| Seq. No. | Structure of Quaternary Cation on Clay | Conc. of Clay in Medium (%) | Chloride Reactant Used, Moles | i-Propanol to Water Ratio$^a$ | X-ray Spacing 001 A | Elemental Composition of Modified Clay, % | | | | | | |
|---|---|---|---|---|---|---|---|---|---|---|---|---|
| | | | | | | Calc. for 100 me/ 100 g dry clay | | | Found | | | |
| | | | | | | C | H | P | C | H | P | Cl |
| 1 | $(C_2H_5)_2P^+(CH_3)C_{18}H_{37}$ | 3 | 0.150$^b$ | 0/1 | 21.6 | 20.54 | 3.75 | 2.30 | 20.80 | 3.75 | 2.20 | 0.18 |
| 2 | $(C_2H_5)_2P^+(CH_3)C_{27}H_{54}$ | 2 | 0.027$^c$ | 1/10 | 24.6 | 26.69 | 4.75 | 2.08 | 25.41 | 4.85 | 2.01 | 0.26 |
| 3 | $(C_2H_5)_2P^+(CH_2CH=CH_2)C_{18}H_{37}$ | 2 | 0.027$^d$ | 0/1 | 23.2 | | | | | | | |
| 4 | $(i$-$C_4H_9)_2P^+(C_2H_5)C_{12}H_{25}$ | 2 | 0.027$^d$ | 0/1 | 21.3 | 19.86 | 3.64 | 2.33 | 20.94 | 4.10 | 2.35 | 0.05 |
| 5 | $(i$-$C_4H_9)_2P^+(C_2H_5)C_{16}H_{33}$ | 2 | 0.054$^d$ | 0/1 | 22.6 | 22.53 | 4.22 | 2.24 | 23.52 | 4.58 | 2.18 | 0.05 |
| 6 | $(i$-$C_4H_9)_2P^+(CH_2CH=CH_2)C_{12}H_{25}$ | 2 | 0.018$^d$ | 1/10 | | 20.57 | 3.60 | 2.31 | 20.73 | 4.01 | 2.33 | 0.31 |

$^a$The isopropanol water ratio of the clay suspension and phosphonium salt solution reactants is generally the same. If the solution has a different solvent ratio it is specificaly stated so in a proper footnote.
$^b$About 7% solution at 50°.
$^c$About 10% solution in 2 to 1 isopropanol water at 50°.
$^d$About 10% solution.

The elemental and X-ray analysis of the products indicated their structure. The interplanar distance of the quaternary diethyl octadecyl phosphonium derivatives (Seq. Nos. 1 and 3) as expected showed little dependence on the third low alkyl group as shown by a comparison with the value for the corresponding triethyl octadecyl phosphonium clay of Table III, Seq. No. 6. Similarly, the interplanar distances of the two ethyl diisobutyl high monoalkyl phosphonium clays (Seq. Nos. 4 and 5) are comparable to those of the corresponding triisobutyl high monoalkyl phosphonium clays (Table V, Seq. Nos. 3 and 5).

sulted in an immediate tremendous thickening of the mixture. A few minutes after the addition, the viscosity decreased. Stirring of the reaction mixture was continued for 45 minutes. Thereafter, the product was isolated in the usual manner.

Elemental analysis: Calculated for 100 miliequivalent phosphonium group,

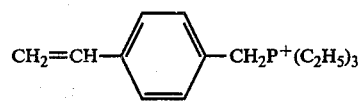

per 100 g dry starting clay: C, 13.62; H, 1.83; P, 2.34; Found: C, 12.02; H, 2.19; P, 2.25, Cl, 0.07. Interplanar spacing of 001 Reflection by X-Ray: 15.7° A.

EXAMPLE 12 — Preparation of Tetraethyl Phosphonium Montmorillonite Clay

To a stirred aqueous suspension of 22.2 g sodium montmorillonite (MCBP) a 5% aqueous solution of 3.65 g (0.02) tetraethyl phosphonium chloride was added at 50° C. so as to obtain a reaction mixture having a 2% concentration of the starting clays. A thickening of the mixture occurred within a few minutes rather than seconds after the addition. After 30 minutes stirring the product was isolated as usual.

Using a 1% aqueous suspension of sodium hectorite, tetraethyl phosphonium hectorite was prepared in a similar manner.

EXAMPLE 13 — Preparation of Tetrabutyl Phosphonium Montmorillonite

To a stirred aqueous suspension of 60 g refined sodium montmorillonite (MCBP) at 50° C., a 10% aqueous solution of 15.93 g (0.054 mole) of tetra-n-butyl phosphonium chloride was added all at once to yield a reaction mixture of 2% starting clay concentration. On mixing an immediate thickening and then in a few minutes the formation of large coarse tetrabutyl phosphonium clay particles occurred. After 30 minutes stirring, the product was isolated in the usual manner.

Elemental analysis: Calculated for 99 me $(C_4H_9)_4P^+$ group per 100 g dry clay: C, 15.42; H, 2.91; P, 2.49. Found: C, 13.24; H, 3.06; P, 2.09.

The same product was prepared in a similar manner, starting with 60 g clay and 20.43 g (0.054 mole) of tetrabutyl phosphonium acetate-acetic acid adduct, $[(n-C_4H_9)_4P^+]CH_3CO_2^-\cdot CH_3CO_2H$.

EXAMPLE 14 — Preparation of Decosyl Trimethyl Phosphonium Laponite XLG Synthetic Clay Laponite XLG from Pfizer is a pure fluorine free synthetic inorganic clay. It is prepared by the removal of electrolyte impurities from Laponite CP which was described by B. S. Neumann and K. G. Sansom in the *Journal of the Society of Cosmetic Chemists* in Volume 21, pages 237 to 258 in 1970. Its formula is $[Si_8Mg_{5.1}Li_{0.6}H_{4.6}O_{24}]^{0.6}Na_{0.6}$. Its cation exchange capacity, as determined using ammonium acetate, is 79 miliequivalents per 100 g.

A clear, viscous colloidal suspension of 25 g Laponite XLG in 700 ml of 2 to 1 water-isopropanol mixture was prepared by stirring for one hour at 50° C. Then a 45° C. solution of 8.4 g. (0.02 m) of docosyl trimethyl phosphonium chloride in 940 ml of the same solvent mixture was added to it fast at 50° C. while stirring. On addition, a moderate degree of further thickening of the mixture occurred. This thickening disappeared in a few minutes and small particles of the white product appeared. After 30 minutes stirring, the phosphonium laponite product was isolated and dried in the usual manner.

Elemental analysis: Calculated for 79 me $C_{22}H_{25}P^+(C_2H_5)_3$ group per 100 g starting laponite clay: C, 18.62; H, 3.38; P, 1.92. Found: C, 19.92; H, 4.10; P, 1.98; Cl < 0.02.

A similar experiment was carried with docosyl trimethyl phosphonium chloride, using it at the 100 miliequivalent per 100 g laponite treatment level to produce an organic clay having a higher percentage of phosphonium moieties.

Elemental analysis: Calculated for 100 me salt per 100 g clay: C, 22.03; H, 3.99; P, 2.28. Found: C, 23.51; H, 4.81; P, 2.39; Cl, 0.09.

EXAMPLE 15 — Preparation of Docosyl Triethyl Phosphonium Laponite XLG Synthetic Clay A colloidal suspension of 24.9 g Laponite XLG in 1120 ml 20% isopropanolic water was prepared in 75 minutes stirring at 50°. To the suspension a 10% solution of 9.13g (0.0197 mole) of docosyl triethyl phosphonium chloride in the same medium was added at a fast rate. The addition resulted in a stronger gel. However, during continued stirring for 30 minutes, the viscosity decreased. This mixture was then filtered by suction at a slow rate because of its gel-like character. After the usual washing, the white solid product was isolated by drying in vacuo.

Elemental analysis: Calculated for 79 me $C_{22}H_{45}P^+(C_2H_5)_3$ per 100 g laponite: C, 20.13; H, 3.62; P, 1.86. Found: C, 21.50; H, 4.18; P, 1.98.

EXAMPLE 16 — Preparation of Docosyl Triethyl Phosphonium Laponite B Synthetic Clay Laponite B from Pfizer is a synthetic clay closely approximating the chemical composition of natural Hectorite. Its percentage composition is: $SiO_2$, 55.9; MgO, 26.7; $Li_2O$, 1.9; F, 8.3; $Na_2O$, 4.3; $Fe_2O_3$, 0.04; CaO, 0.10; $SO_3$, 0.05; $CO_2$, 0.24; $H_2O$ (Structural), 3.60. Its cation exchange capacity is in the range of 80 to 110 me per 100 g.

To a hazy, viscous colloidal suspension of 19.7 g Laponite B in 872 ml 20% isopropanol in water mixture at 50° C., a 10% solution of 9.13 g (0.0197 mol) of docosyl triethyl phosphonium chloride in the same solvent medium was added at a fast rate. An immediate reaction was indicated by the turn of the mixture to a white suspension. However, there was no great change in viscosity of the mixture at any time during the reaction. After 30 minutes stirring at 50° C., the viscous mixture was filtered with suction with difficulty. The white, solid product was then washed and dried in the usual manner.

Elemental analysis: Calculated for 100 miliequivalent $C_{22}H_{45}P^+(C_2H_5)_3$ per 100 g clay: C, 23.94; H, 4.31; P, 2.21. Found: C, 24.28; H, 4.25; P, 2.27; Cl, 0.33.

EXAMPLE 17 — Preparation of 4-Vinylbenzyl Triethyl Phosphonium Kaolinite

The kaolinite used in this reaction is a hydrated aluminum silicate. It is a white china clay processed by fractional centrifugation to have a median particle size of 0.55 microns. A 20% aqueous slurry of this clay has a pH of 4.2 to 5.2. A 70% slurry has a Brookfield viscosity of 430 centipoise at 10 rpm. Its oil adsorption is 42% by the Garden Colman technique.

Elemental composition, %: $Al_2O_3$, 38.38; $SiO_2$ (combined), 45.30; $H_2O$ (combined, ignition loss at 950° C.), 13.97; $Fe_2O_3$, 0.30; $TiO_2$, 1.44; CaO, 0.05; MgO, 0.25; $Na_2O$, 0.27, $K_2O$, 0.04.

As a dispersant for the hydrite in water, either sodium hexametaphosphate and sodium carbonate from Mill Chem (MC) or ethylenediamine (EDA) was used. The general procedure for the kaolin dispersion and reaction with the phosphonium salt was the following.

Using an Osterizer, high speed mixer 300 ml water was blended with the proper amounts of one of the above dispersants. Then with continued stirring, 250 g Hydrite 10 was added. After the addition, stirring was continued at a high speed for 5 minutes. The resulting kaolin dispersion was transferred into a beaker, using distilled water to wash the Osterizer and to dilute the dispersion to a 10-15% solids in water level. The contents of the beaker were then mixed with a mechanical stirrer for 3-5 minutes and checked for pH and dispersion quality. The pH of the Calgon dispersions was 6.0 while that of the EDA dispersions was 9.8.

To the above dispersion, either 3.125 g (1.25% salt, i.e. 0.15% phosphorus) or 6.25 g (2.5% salt, i.e. 0.3% phosphorus) of 4-vinylbenzyl triethyl phosphonium chloride salt was added with stirring. Stirring was continued for several minutes and the pH monitored. Then the mixture was either kept at room temperature for 10 minutes or slowly heated to 65° C. and held there for 10 minutes while stirring. The solids were then filtered with suction and dried at 100°-110° C. to provide the products.

The results show that using 0.15% phosphorus in the form of the phosphonium salt reactant, a complete reaction occurs with the sodium hexametaphosphate dispersed aqueous kaolinite independent of the reaction temperature. Doubling the amount of phosphonium reactant does not increase the 0.15% phosphorus content of the product. Using ethylenediamine instead of sodium hexametaphosphate reduces the phosphorus content to about 0.1% regardless of the reactant ratio and reaction temperature and the bisicity of the reaction mixture.

EXAMPLE 18 — Preparation of 14-Diphenylphosphinotetradecyl Triethyl Phosphonium Montmorillonite and Its Complexing with 1,5-Cyclooctadiene Rhodium Chloride To a stirred nitrogenated 0.85% suspension of 18.5 g dry (20.5g wet) MCBP in 50% aqueous isopropanol, an 8.5% solution under nitrogen of 10g (0.019 m) of 14-diphenylphosphinotetradecyl triethyl phosphonium chloride, also in 50% aqueous isopropanol was added during the course of a minute. Immediate reaction was indicated by a typical thickening of the mixture. After 30 minutes additional stirring, the product was filtered off with suction, washed and dried at 60° in the usual manner.

The above phosphinoalkyl phosphonium montmorillonite was ball-milled and screened using a 200 mesh screen. Of the screened phosphonium clay, 16.3 g was dispersed with stirring under nitrogen in a 0.25% benzene solution of 1.36 g (0.01 m) of 1,5-cyclooctadiene rhodium chloride dimer. A stable suspension resulted which was filtered with suction and washed three times with 50 ml nitrogenated benzene to provide the bright yellow solid clay complex product.

After drying overnight at room temperature at 0.1 m m. the product was analyzed for rhodium and phosphorus. The percentage values found were Rh, 1.94; P, 2.77. These values show that almost one atom rhodium was complexed per two phosphine moieties. The degree of rhodium removal from the benzene by complexation was about 60%.

EXAMPLE 19 — Preparation of bis 3-Hydroxypropyl Octadecyl Primary Isobutyl Phosphonium Montmorillonite To a stirred nitrogenated 2.25% aqueous suspension of 25 g (0.0225 mole equivalent) MCBP at 50°, at 10% aqueous solution of 11.1g (0.0225 mole) 3-hydroxypropyl octadecyl primary isobutyl phosphonium chloride, also at 50°, is added all at once. A thickening of the reaction mixture and a swelling of the clay occurred within a minute of the addition. During the subsequent 30 minute stirring, the viscosity decreased. Thereafter, the mixture was promptly filtered with suction and washed with three 250 ml portions of water in 15 minutes. The filter cake was then dried for 72 hours at room temperature under 0.1 mm pressure to provide the dry product in a quantitative yield.

The ball milled product of less than 200 mesh size swells in styrene and is an effective gellant for alkyd resins.

EXAMPLE 20 — Preparation of bis-3-Hydroxypropyl Docosyl Primary Isobutyl Phosphonium Montmorillonite Bis-3-hydroxypropyl docosyl primary isobutyl phosphonium chloride (12.2g, 0.0225 m) was reacted with 25 g (0.0225 mole equivalent) MCBP in the manner described in the previous example to yield the corresponding phosphonium montmorillonite gellant.

EXAMPLE 21 — Preparation of Bis-3-Dimethylaminopropyl Dodecyl Primary Isobutyl Phosphonium Montmorillonite Bis-3-dimethylaminopropyl dodecyl primary isobutyl phosphonium chloride (10.5g, 0.0225 m) was reacted with 25 g (0.0225 mole equivalent) MCBP in the manner described in Example 18 to yield the corresponding phosphonium montmorillonite.

EXAMPLE 22 — Preparation of Tris-cyanoethyl Dodecyl Phosphonium Montmorillonite Tris-cyanoethyl dodecyl phosphonium bromide (10g, 0.0225 m) was reacted with 25g (0.0225 mole equivalent) MCBP in the manner described in Example 18 to yield the corresponding phosphonium montmorillonite.

THE METHODS USED TO DETERMINE GELLING ABILITY

All the gel test methods give somewhat different results if organic clays of various particle size are used. Therefore, the dry, ball milled clays were all passed through a 200 mesh screen before testing.

The Styrene Swelling Test

A two gram organic clay sample was slowly added using a spatula to 100 ml polymerization grade styrene. The styrene was contained in a 100 ml measuring cylinder of about 2.5 cm diameter. On the addition of the clay gelling agents, a spontaneous gelling occurred. The resulting gel volume of the clays was severalfold of the original by the time they fell to the bottom of the cylinder. The volume of the resulting bottom gel "phase" was read after 15 minutes, 2 hours and 24 hours.

The Toluene Gel Strength Test

To 294 g toluene placed into a Waring blender, 6 g of tetraalkyl phosphonium clay is added in 45 seconds while it is stirred at a rate of about 10,000 rpm (transformer setting 25). The resulting mixture is then stirred at 15,000 rpm for 90 seconds (Transformer setting 100). The stirring rate is then reduced to 13,000 and 2.3 ml polar additive, consisting of 95% commercial (i.e., 99%) methanol and 5% distilled water is added over 30 seconds. The speed is then again increased to 15,000 rpm and the stirring continued for a further 3 minutes.

The gel is then poured into a pint jar which is subsequently rocked and swirled for 30 seconds to remove most of the air bubbles. The jar is then capped tight and put into a 25° C. water bath. After fifteen minutes and 24 hours, viscosity readings are taken using a Brookfield viscometer with a number three spindle. The spindle is inserted to the near side of the jar and then moved to the center. Then viscosity readings are taken from low to high stirring rates: at 10 rpm after 40 seconds at this speed, at 20 rpm after 30 seconds, at 50 rpm after 20 seconds and at 100 rpm after 15 seconds. After the viscosity readings, the temperature in the rear side of jar is usually about 30° C. and at the center 35° C.

After the 10 minute reading, the jar is capped and set in a 25° C. water bath until the 24 hour reading.

The Alkyd Resin Gel Test

Alkyd resins are in general, polyesters derived from fatty acids, polyols such glycerol or glycol, and dicarboxylic acids, usually phthalic anhydride. The resins used in the present tests were long oil alkyd resins, which are most commonly used for general purpose industrial coatings. They were obtained from Reichhold Chemical under the name Beckosol P-296-70 with a computer code number 10-045. The product contains 30% mineral spirits as a solvent. The solid resin (70% is derived using about 65% soybean oil, 24% phthalic anhydride and 11% glycerol. As such, the product meets federal specification, classification TTR 2660A, Type Class A, vinyl compatible. Its Gardner-Holdt viscosity is Y-$Z_2$. The viscosity of the products supplied was apparently significantly different on the Brookfield scale.

In the test procedure, 1.25 g of organic clay is slowly added to 88 g resin, while stirring it with a high speed, i.e., high shear mixer (with a drill press equipped with a circular Cowle's blade). After mixing for about two to five minutes, a polar solvent mixture consisting of 95% propylene carbonate and 5% water is added in an amount equalling 33% of the clay while stirring to give optimum dispersion and highest viscosity. Thereafter, stirring is continued for an additional five minutes. The resulting gel is then thinned using a solvent, i.e., 10 g odorless mineral spirit, to reduce the viscosity. Viscosity measurements of the resulting mixtures are made in 18 to 24 hours after the air bubbles formed during the stirring rose out of the liquid gels.

In the alkyd resin gel tests, three batches of Beckosol P-296-70 were used. Their viscosity characteristics, as determined by the Brookfield viscosimeter, were somewhat different as indicated by the following tabulation:

| Batch Identification of Resin Beckosol P-296-70 | Brookfield Viscosities, cps of Long Oil Alkyd Resins After 18–24 Hours (at Various Stirring Rates, rpm) | | | |
|---|---|---|---|---|
| | (10) | (20) | (50) | (100) |
| A | 2800 | 3000 | 3120 | 3200 |
| B | 2000 | 2200 | 2400 | 2400 |
| C | 2400 | 2500 | 2640 | 2620 |

The different batches of the resin showed different responses to the tetraalkyl phosphonium clay gellants. Therefore, strictly speaking, the data are comparable only when the same batch of resin was used.

The response of these resins to organic clay gellants was determined using available commercial quaternary dimethyl dihydrogenated tallow ammonium clays, as standards. The Astratone 40 standard is manufactured by the Georgia Kaolin Co. starting with refined sodium montmorillonite, basically the same clay which was used in our Examples 3–11. The Bentone 38 standard is manufactured by N. L. Industries from refined sodium hectorite, a clay similar to the one used in Example 1. The effectiveness of these two ammonium clays in the three batches of alkyd resin was as shown by the following tabulation:

| Dimethyl tallow Ammonium Clay | Di-Batch Identification of Resin Beckosol P-296-70 | Brookfield Viscosities, of Long Oil Alkyd Resins After 18–24 Hrs. At Various Stirring Rates, (rpm) | | | |
|---|---|---|---|---|---|
| | | (10) | (20) | (50) | (100) |
| Astratone-40 | A | 6000 | 5400 | 5120 | 4940 |
| Bentone-38 | A | 6800 | 6200 | 5680 | 5320 |
| Astratone-40 | B | 3200 | 3100 | 3040 | 2960 |
| Bentone-38 | B | 4400 | 4000 | 3760 | 3540 |
| Astratone-40 | C | 3400 | 3400 | 3280 | 3120 |
| Bentone-38 | C | 4400 | 4200 | 3920 | 3740 |

EXAMPLE 18 — Gelling Effectiveness of Higher Monoalkyl Trimethyl and Triethyl Phosphonium Montmorillonites The swelling of styrene and the gelling of toluene and a long oil alkyd resin (C) by the quaternary higher monoalkyl phosphonium clays of Example 3, Table III was studied in routine laboratory tests. The results obtained are shown in Table XI.

Overall, the data show that these mono- $C_{14-20}$ alkyl phosphonium clays are effective gelling agents. The styrene swelling showed no definite correlation with the length of the higher n-alkyl group. The toluene and alkyd resin gelling seemed to be at a maximum in the $C_{14-16}$ alkyl range (Seq. Nos. 5 and 6). In the case of the dodecyl

TABLE XI
STYRENE SWELLING, TOLUENE AND ALKYD RESIN GELLING EFFICIENCY OF HIGHER MONOALKYL TRIMETHYL AND TRIETHYL PHOSPHONIUM MONTMORILLONITES
$[CH_3(CH_2O)_{n-1}P^+C_mH_{2m+1}]$ Clay$^-$; m = 11–20

| Seq. No. | Structure of Quaternary Cation in Clay | Styrene Swell Ml. | | Brookfield Viscosities, cps, At Various Stirring Rates (rpm) | | | | | | | | | | | | Batch of Alkyd Used |
|---|---|---|---|---|---|---|---|---|---|---|---|---|---|---|---|---|
| | | | | 2% Solids in Toluene | | | | | | | | 1.4% Solids in Alkyd Resin | | | | |
| | | | | After 15 Mins. | | | | After 24 Hrs. | | | | After 18–24 Hrs. | | | | |
| | | 2Hr | 24Hr | (10) | (20) | (50) | (100) | (10) | (20) | (50) | (100) | (10) | (20) | (50) | (100) | |
| 1 | [(CH$_3$)$_3$P$^+$C$_{11}$H$_{23}$] | | | 42 | 19 | 10 | 10 | Gel Unstable | | | | 2600 | 2600 | 2880 | 2860 | A |
| 2 | [(CH$_3$)$_3$P$^+$C$_{14}$H$_{29}$] | 28 | 28 | | | | | | | | | 4000 | 4400 | 4240 | 4040 | A |
| 3 | [(CH$_3$)$_3$P$^+$C$_{20}$H$_{41}$] | 31 | 30 | 1320 | 740 | 304 | 152 | 1600 | 720 | 304 | 176 | 7600 | 7000 | 5680 | 5640 | A |
| 4 | [(C$_2$H$_5$)$_3$P$^+$C$_{12}$H$_{25}$] | 20 | 20 | 392 | 188 | 77 | 50 | 178 | 90 | 43 | 31 | 7200 | 6200 | 5440 | 5040 | A |
| 5 | [(C$_2$H$_5$)$_3$P$^+$C$_{16}$H$_{33}$] | 29 | 28 | 1968 | 900 | 387 | 179 | 1416 | 672 | 298 | 204 | 9600 | 8000 | 6640 | 6060 | A |
| 6 | [(C$_2$H$_5$)$_3$P$^+$C$_{18}$H$_{37}$] | 30 | 29 | 1816 | 880 | 326 | 171 | 1344 | 672 | 288 | 157 | 10,000 | 8000 | 6960 | 6160 | A |
| 7 | [(C$_2$H$_5$)$_3$P$^+$C$_{20}$H$_{41}$] | 26 | 24 | 1320 | 612 | 251 | 126 | 784 | 428 | 210 | 116 | 5200 | 4800 | 4320 | 4140 | A | triethyl phosphonium clay (Seq. No. 4), a good alkyl resin gelling but poor toluene gelling was observed. The behavior of the docosyl trimethyl and triethyl phosphonium derivatives (Seq. Nos. 3 and 7) was similar. However, the viscosity of the trimethyl phosphonium gel increased with time while that of the triethyl derivative decreased.

creases as the lower trialkyl groups increase from trimethyl to tributyl (from Seq. No. 1 to 5). The same trend is observed with regard to their efficiency in gelling a long oil alkyl resin. The trimethyl compound has little effect in gelling the alkyd (Seq. No. 1).

TABLE XII

STYRENE SWELLING, TOLUENE AND ALKYD RESIN GELLING OF TRI-n-BUTYL AND TRI-i-BUTYL PHOSPHONIUM MONTMORILLONITES
$[(C_4H_9)_3P^+C_mH_{2m+1}]$ Clay$^-$; m = 12-18

| Seq. No. | Structure of Quaternary Cation on Clay | Styrene Swell Ml. 2 Hr | Styrene Swell Ml. 24 Hr | Brookfield Viscosities, cps, At Various Stirring Rates, (rpm) 2% Solids in Toluene After 15 Mins. (10) | (20) | (50) | (100) | 2% Solids in Toluene After 24 Hrs. (10) | (20) | (50) | (100) | 1.4% Solids in Alkyd Resin After 18-24 Hrs. (10) | (20) | (50) | (100) | Batch of Alkyd Used |
|---|---|---|---|---|---|---|---|---|---|---|---|---|---|---|---|---|
| 1 | $[(n-C_4H_9)_3P^+C_{12}H_{25}]$ | 30 | 30 | 440 | 196 | 80 | 43 | 240 | 120 | 46 | 49 | 7600 | 6800 | 6000 | 5440 | A |
| 2 | $[(n-C_4H_9)_3P^+C_{16}H_{33}]$ | 32 | 32 | 416 | 184 | 77 | 42 | 184 | 76 | 38 | 17 | 14000 | 11000 | 8400 | 7200 | A |
| 3 | $[(i-C_3H_9)_3P^+C_{12}H_{25}]$ | | | 1120 | 580 | 172 | 84 | 840 | 430 | 172 | 94 | 5200 | 4800 | 4560 | 4300 | C |
| 4 | $[(i-C_4H_9)_3P^+C_{14}H_{29}]$ | | | 680 | 260 | 104 | 60 | 440 | 220 | 104 | 64 | 5800 | 5500 | 4960 | 4560 | C |
| 5 | $[(i-C_4H_9)_3P^+C_{16}H_{33}]$ | | | 760 | 360 | 136 | 74 | 660 | 320 | 152 | 88 | 5000 | 4700 | 4480 | 4200 | C |
| 6 | $[(i-C_4H_9)_3P^+C_{18}H_{37}]$ | 35 | 34 | 1200 | 480 | 176 | 96 | 496 | 248 | 128 | 68 | 5200 | 4700 | 4200 | 3800 | B |

TABLE XIII

STYRENE SWELLING, TOLUENE AND ALKYD RESIN GELLING EFFICIENCY OF DOCOSYL LOWER TRIALKYL PHOSPHONIUM MONTMORILLONITES
$[(C_nH_{2n+1})_3P^+C_{22}H_{45}]$ Clay$^-$; n-1-4

| Seq. No. | Structure of Quaternary Cation on Clay | Styrene Swell Ml. 2Hr | Styrene Swell Ml. 24Hr | 2% Solids in Toluene After 15 Mins. (10) | (20) | (50) | (100) | 2% Solids in Toluene After 24 Hrs. (10) | (20) | (50) | (100) | 1.4% Solids in Alkyd Resin After 18-24 Hrs. (10) | (20) | (50) | (100) | Batch of Alkyd Used |
|---|---|---|---|---|---|---|---|---|---|---|---|---|---|---|---|---|
| 1 | $[(CH_3)_3P^+C_{22}H_{45}]$ | 30 | 30 | 232 | 92 | 42 | 29 | 352 | 164 | 83 | 62 | 4400 | 4300 | 4300 | 4500 | A |
| 2 | $[(C_2H_5)_3P^+C_{22}H_{45}]$ | 32 | 32 | 720 | 560 | 208 | 104 | 1000 | 560 | 208 | 104 | 7600 | 7000 | 5840 | 5680 | A |
| 3 | $[(n-C_3H_7)_3P^+C_{22}H_{45}]$ | 41 | 40 | 760 | 340 | 133 | 70 | 272 | 144 | 70 | 45 | 7600 | 7000 | 6400 | 6040 | A |
| 4 | $[(i-C_3H_7)_3P^+C_{22}H_{45}]$ | 44 | 42 | 600 | 268 | 114 | 66 | 592 | 292 | 134 | 76 | | | | | |
| 4 | $[(n-C_4H_9)_3P^+C_{22}H_{45}]$ | 47 | 47 | 224 | 100 | 54 | 34 | 256 | 124 | 64 | 35 | 14000 | 11000 | 8720 | 7360 | A |

EXAMPLE 19 — Gelling Effectiveness of Higher Monoalkyl Tributyl Phosphonium Montmorillonites The swelling of styrene and the gelling of toluene and some long oil alkyl resins of the higher monoalkyl tributyl monoalkyl phosphonium clays of Example 4, Table IV, was determined as shown in Table XII.

The data in general indicate that all clay derivatives prepared are effective gelling agents. It is interesting to note that the higher alkyl tri-n-butyl phosphonium clays are less effective in gelling toluene than the corresponding tri-i-butyl compounds (Seq. Nos. 1 and 2 versus 3 and 5). The dodecyl tri-i-butyl phosphonium clay is the best compound for gelling toluene (Seq. No. 3).

EXAMPLE 20 — Gelling Effectiveness of Docosyl Lower Trialkyl Phosphonium Montmorillonite Clays The docosyl tri-$C_{1-4}$-alkyl phosphonium clays of Example 5, Table V were evaluated for their gelling efficiency in routine tests. The results are shown in Table XIII.

The data show that the docosyl lower trialkyl compounds are all gellants. Their swelling in styrene in-

EXAMPLE 21 — Gelling Effectiveness of Higher Dialkyl Dimethyl and Diethyl Phosphonium Montmorillonite Clays The di-$C_{8-18}$-alkyl phosphonium clays of Example 6, Table VI were evaluated for swelling and gelling in the usual routine tests. The data obtained are shown in Table XIV.

The results indicate that the higher dialkyl phosphonium clays of Table XIV are surprisingly less effective in gelling toluene than the monoalkyl derivatives of Table XII. The alkyd resin gelling effectiveness of the higher dialkyl compounds is comparable to that of the higher monoalkyl compounds.

TABLE XIV

STYRENE SWELLING, TOLUENE AND ALKYD RESIN GELLING EFFICIENCY OF HIGHER DIALKYL DIMETHYL AND DIETHYL PHOSPHONIUM MONTMORILLONITES
$(C_rH_{2r+1})_2P^+(CH_2)_{0-1}CH_3$; r = 8-18

| Seq. No. | Structure of Quaternary Cation on Clay | Styrene Swell, ml (After Hrs) (2) | (24) | 2% Solids in Toluene After 15 Mins. (10) | (20) | (50) | (100) | 2% Solids in Toluene After 24 Hrs. (10) | (20) | (50) | (100) | 1.4% Solids in Alkyd Resin After 18-24 Hrs. (10) | (20) | (50) | (100) | Batch of Alkyd Used |
|---|---|---|---|---|---|---|---|---|---|---|---|---|---|---|---|---|
| 1 | $[(CH_3)_2P^+(C_8H_{17})_2]$ | 23 | 23 | 232 | 100 | 45 | 25 | Gel Unstable | | | | 7600 | 6800 | 5680 | 5600 | A |
| 2 | $[(CH_3)_2P^+(C_{10}H_{21})_2]$ | 19 | 19 | 328 | 152 | 64 | 37 | 160 | 96 | 27 | 14 | 12000 | 9600 | 7760 | 6840 | A |
| 3 | $[(CH_3)_2P^+(C_{12}H_{25})_2]$ | 23 | 23 | 120 | 56 | 26 | 24 | Gel Unstable | | | | 11600 | 10000 | 8320 | 7300 | A |
| 4 | $[(C_2H_5)_2P^+(C_{18}H_{37})_2]$ | 30 | 30 | 240 | 208 | 91 | 52 | Gel Unstable | | | | 9600 | 8000 | 6880 | 6440 | A |

EXAMPLE 22 — Gelling Efficiency in Alkyd Resin of Quaternary Higher Trialkyl Phosphonium Montmorillonite Clays The quaternary tri-$C_{6-10}$-alkyl phosphonium clays of Example 7, Table VII were examined for their gelling efficiencies in the previously described routine tests. All the clays of this group were found ineffective gellants for toluene. The observed toluene viscosities were below 200 cps. However, some of the products were effective in gelling a long oil alkyd resin as shown by Table XV.

The results clearly demonstrate the superior gellant effectiveness of the methyl and ethyl trioctyl phosphonium clays in an alkyd resin among the quaternary higher trialkyl phosphonium clays tested. (Seq. Nos. 2 and 3). The gellant effectiveness of the trioctyl group is rapidly decreased as the chain length of the fourth alkyl group is increased beyond two carbons (Seq. Nos. 3 versus 4 and 5). As the chain length of the fourth alkyl group is increased beyond four carbons, quaternary trioctyl phosphonium clays possess no gellant capacity in the alkyd resin. (Seq. Nos. 6 and 7). Similarly, the benzyltrioctyl clay product is not an alkyd gellant either (Seq. No. 8).

Another surprising finding is the rapid decrease in gelling capacity when the trialkyl group is decreased to six carbons or increased to ten carbons per chain. Both the methyl trihexyl and methyl tridecyl phosphonium clays are significantly less effective alkyd gellants than the corresponding methyl trioctyl quaternary clay derivates (Seq. Nos. 4 and 7 versus 2).

TABLE XV

GEL STRENGTH IN AN ALKYD RESIN OF QUATERNARY HIGHER TRI-$C_{6-10}$-ALKYL PHOSPHONIUM MONTMORILLONITE CLAYS
[$(C_jH_{2j+1})_3P^+C_kH_{2k+1}$] Clay$^-$; j = 6-10; k = 1-6

| Seq. No. | Structure of Quarternary Cation | Brookfield Viscosities. cps. After 18-24 Hrs. of Alkyd Resin Containing 1.4% Clay Solids (at Various Stirring Rates rpm) | | | |
|---|---|---|---|---|---|
| | | (10) | (20) | (50) | (100) |
| 1 | [$(C_6H_{13})_3P^+CH_3$] | 3200 | 3400 | 3360 | 3400 |
| 2 | [$(C_8H_{17})_3P^+CH_3$] | 5600 | 5200 | 4960 | 4560 |
| 3 | [$(C_8H_{17})_3P^+C_2H_5$] | 6000 | 5400 | 4920 | 4560 |
| 4 | [$(C_8H_{17})_3P^+n$-$C_3H_7$] | 4000 | 3600 | 3440 | 3080 |
| 5 | [$(C_8H_{17})_3P^+n$-$C_9H_9$] | 3600 | 3500 | 3280 | 3120 |
| 6 | [$(C_8H_{17})_3P^+n$-$C_5H_{11}$] | 2400 | 2600 | 2760 | 2620 |
| 7 | [$(C_8H_{17})_3P^+n$-$C_6H_{13}$] | 2400 | 2500 | 2640 | 2620 |
| 8 | [$(C_8H_{17})_3P^+CH_2$—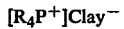] | 2600 | 2700 | 2880 | 2920 |
| 9 | [$(C_{10}H_{21})_3P^+CH_3$] | 3600 | 3200 | 3120 | 2840 |

The adverse effect of increasing the carbon number of the fourth alkyl substituent of quaternary trioctyl phosphonium clays is especially interesting since this structural change of the phosphonium groups does not affect the interplanar distance of their clay derivatives. It is proposed that in the case of these and similar higher trialkyl phosphonium clays the decreased gelling efficiency is due to increased steric crowding, which inhibits the polar interactions involved in the gelling process. The way steric factors may play a role is indicated by the proposed position of the hexyl trioctyl phosphonium group in the interplanar space. As shown in Example 7, FIG. 1, the hexyl group is oriented parallel to the surface and as such its dimensions will influence the degree of the polar interactions of polar additives or polar fluids to be gelled with the phosphonium and silicate groups. Once such polar interactions are completely blocked, no gelling will occur.

What is claimed is:

1. Tetraalkyl phosphonium clays of the formula:

$$[R_4P^+]Clay^-$$

wherein the four R groups are $C_1$-$C_{100}$ aliphatic hydrocarbyl radicals selected in such a manner that at least one of the R groups is substituted.

2. The composition of claim 1 wherein the Clay$^{-1}$ is a negatively charged aluminosilicate of the layer and chain type structure.

3. The composition of claim 2 wherein the aliphatic hydrocarbyl radicals are alkyl radicals at least one of which is substituted and, at least one of which contains at least 8 carbon atoms.

4. The composition of claim 3 wherein the substituent is on an alkyl radical other than the alkyl radical containing at least 8 carbon atoms.

5. The composition of claim 1 wherein the substituent on the R groups is selected from the group consisting of phosphino, amino, cyano and hydroxy substituents and combinations thereof.

6. Tetraalkyl phosphonium clays of the formula:

$$\{R_xP^+[QZ]_y\}Clay^-$$

wherein R is a $C_1$-$C_{100}$ monovalent aliphatic hydrocarbyl radical, Q is a $C_1$-$C_{100}$ divalent aliphatic hydrocarbyl radical, Z is a heteroatomic radical containing up to 40 carbon atoms and x and y are 1 to 3 providing that x + y equal 4.

7. The composition of claim 6 wherein Q is a $C_1$-$C_{40}$ divalent aliphatic hydrocarbyl radical and Z is a heteroatomic radical containing up to 40 carbon atoms selected from the group consisting of phosphino, amino, cyano and hydroxy groups.

8. The composition of claim 6 wherein Clay$^-$ is a negatively charged layered aluminosilicate.

9. The composition of claim 8 wherein the negatively charged layered aluminosilicate is a negatively charged montmorillonite.

10. The composition of claim 6 wherein at least one R is a $C_8$-$C_{100}$ aliphatic hydrocarbyl radical and Clay$^-$ is a negatively charged aluminosilicate.

11. The composition of claim 10 wherein at least one R group is allyl.

12. The composition of claim 10 wherein the $C_1$-$C_{100}$ aliphatic hydrocarbyl radical R groups are selected from the group consisting of alkyl and alkenyl.

13. The composition of claim 6 wherein Q is selected from the group consisting of alkylene and alkenylene.

14. Diphenylphosphino substituted tetraalkyl phosphonium clays of the formula:

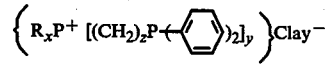

wherein R is a $C_1$-$C_{100}$ monovalent aliphatic hydrocarbyl radical, x and y are 1 to 3, providing that x + y equal 4 and z is 1 to 40.

15. The compositions of claim 14 wherein Z is 6 to 14.

16. 14-Diphenylphosphinotetradecyl triethyl phosphonium montmorillonite.

17. Dialkylamino substituted tetraalkyl phosphonium clays of the formula:

$$\{R_xP^+[(CH_2)_zN(C_qH_{2q+1})_2]_y\}Clay^-$$

wherein R is a $C_1$-$C_{100}$ monovalent aliphatic hydrocarbyl radical; q is 0 to 18; x and y are 1 to 3, providing that x plus y equal 4; z is 1 to 40.

18. The compositions of claim 17 wherein q is 1 to 18.

19. The compositions of claim 17 wherein z is 3.

20. Bis-dimethylaminopropyl dodecyl isobutyl phosphonium montmorillonite.

21. Cyano substituted tetraalkyl phosphonium clays of the formula:

$$\{R_xP^+[(CH_2)_zCN]_y\}Clay^-$$

wherein R is a $C_1$–$C_{100}$ monovalent aliphatic hydrocarbyl radical; x and y are 1 to 3, providing that x plus y are 4; z is 1 to 40.

22. The compositions of claim 21 wherein z is 2.

23. Tris-cyanoethyl dodecyl phosphonium montmorillonite.

24. Hydroxy substituted tetraalkyl phosphonium clays of the formula:

$$\{R_xP^+[(CH_2)_zOH]_y\}Clay^-$$

wherein R is a $C_1$–$C_{100}$ monovalent aliphatic hydrocarbyl radical; x and y are 1 to 3, providing that x plus y are 4; z is 1 to 40.

25. The compositions of claim 24 wherein z is 1 to 3.

26. Bis-hydroxypropyl octadecyl isobutyl phosphonium montmorillonite.

27. Bis-hydroxypropyl docosyl isobutyl phosphonium montmorillonite.